US012705663B2

(12) United States Patent
LeTensorer et al.

(10) Patent No.: US 12,705,663 B2
(45) Date of Patent: Aug. 11, 2026

(54) AI PERSONAL FRAGRANCE CONSULTATION AND FRAGRANCE SELECTION/RECOMMENDATION

(71) Applicant: Coty Inc., New York, NY (US)

(72) Inventors: Yoann LeTensorer, Paris (FR); Shanna Weinblatt, New York, NY (US); Sophie Raviot-Derrien, Versoix (CH); Michael John Baker, Williston, VT (US)

(73) Assignee: Coty Inc., New York, NY (US)

( * ) Notice: Subject to any disclaimer, the term of this patent is extended or adjusted under 35 U.S.C. 154(b) by 50 days.

(21) Appl. No.: 18/837,851

(22) PCT Filed: Feb. 15, 2023

(86) PCT No.: PCT/US2023/062648

§ 371 (c)(1),
(2) Date: Aug. 12, 2024

(87) PCT Pub. No.: WO2023/159056

PCT Pub. Date: Aug. 24, 2023

(65) Prior Publication Data

US 2026/0120162 A1 Apr. 30, 2026

Related U.S. Application Data

(60) Provisional application No. 63/385,082, filed on Nov. 28, 2022, provisional application No. 63/310,493, filed on Feb. 15, 2022.

(51) Int. Cl.
*G06Q 30/00* (2023.01)
*G06Q 10/40* (2026.01)
(Continued)

(52) U.S. Cl.
CPC ......... *G06Q 30/0631* (2013.01); *G06Q 10/40* (2026.01); *G06Q 30/0282* (2013.01);
(Continued)

(58) Field of Classification Search
None
See application file for complete search history.

(56) References Cited

U.S. PATENT DOCUMENTS 10,977,710 B2 * 4/2021 Axelsson ........... G06Q 30/0631
11,514,085 B2 * 11/2022 Kenedy ................ G06F 16/951
(Continued)

FOREIGN PATENT DOCUMENTS

CN 119013682 11/2024
NL 2034153 A 8/2023
(Continued)

OTHER PUBLICATIONS

"International Application Serial No. PCT/US2023/062648, International Search Report mailed Apr. 12, 2023", 2 pgs.
(Continued)

*Primary Examiner* — Mila Airapetian
(74) *Attorney, Agent, or Firm* — Schwegman Lundberg & Woessner, P.A.

(57) ABSTRACT

Data is collected related to a plurality of individuals, and which is used to identify whether any of the data are probable predictors of the individuals' preference for one or more fragrances. These predictors are then used to provide recommendations of one or more fragrances to one or more individuals.

19 Claims, 23 Drawing Sheets

(51) Int. Cl.

| | |
|---|---|
| ***G06Q 30/0282*** | (2023.01) |
| ***G06Q 30/0601*** | (2023.01) |
| ***G06V 40/16*** | (2022.01) |
| ***G16B 20/00*** | (2019.01) |

(52) U.S. Cl.

CPC ....... *G06Q 30/0643* (2013.01); *G06V 40/171* (2022.01); *G06V 40/176* (2022.01); *G16B 20/00* (2019.02)

(56) References Cited

U.S. PATENT DOCUMENTS

| | | | | |
|---|---|---|---|---|
| 2013/0117137 | A1* | 5/2013 | Klein | G07F 17/26<br>705/16 |
| 2016/0042428 | A1* | 2/2016 | Gou | G06Q 30/0631<br>705/26.7 |
| 2019/0253514 | A1* | 8/2019 | Yankovich | G06Q 10/083 |
| 2019/0371028 | A1* | 12/2019 | Harrises | G02B 27/0172 |
| 2020/0364588 | A1* | 11/2020 | Knox | H04L 67/565 |
| 2021/0248656 | A1* | 8/2021 | Makowsky | G06Q 30/0621 |
| 2021/0406983 | A1 | 12/2021 | Lee et al. | |
| 2023/0252838 | A1* | 8/2023 | Yuan | G06Q 30/0621<br>235/381 |
| 2023/0334552 | A1* | 10/2023 | Levin | G16H 20/10 |
| 2024/0249504 | A1* | 7/2024 | Yu | G06N 3/0464 |

FOREIGN PATENT DOCUMENTS

| | | | |
|---|---|---|---|
| NL | 2034153 | B1 | 10/2023 |
| WO | WO-2019183612 | A1 | 9/2019 |
| WO | WO-2023159056 | A1 | 8/2023 |

OTHER PUBLICATIONS

"International Application Serial No. PCT/US2023/062648, Written Opinion mailed Apr. 12, 2023", 5 pgs.

"Netherlands Application Serial No. 2034153, Office Action mailed Sep. 14, 2023", w/o English Translation, 2 pgs.

"Netherlands Application Serial No. 2034153, Response filed Sep. 28, 2023 to Office Action mailed Sep. 14, 2023", W/O English Translation of Claims, 7 pgs.

"Netherlands Application Serial No. 2034153, Search Report mailed Jul. 10, 2023", W/English Translation, 8 pgs.

"International Application Serial No. PCT US2023 062648, International Preliminary Report on Patentability mailed Aug. 29, 2024", 7 pgs.

* cited by examiner

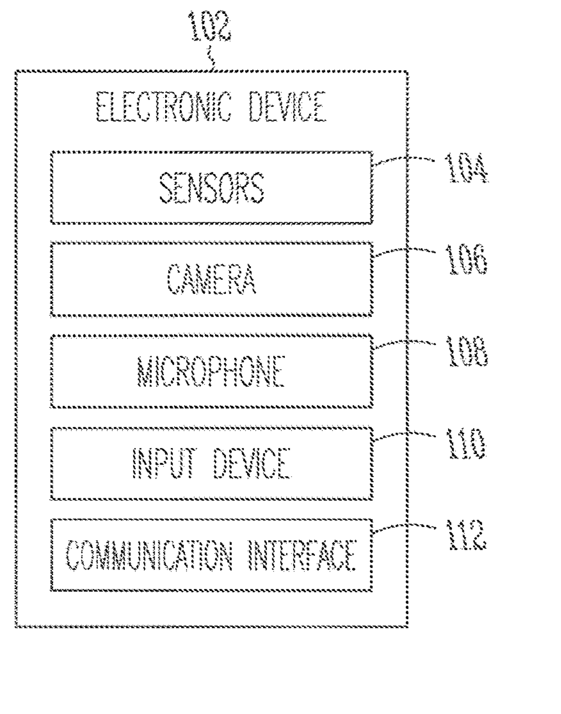
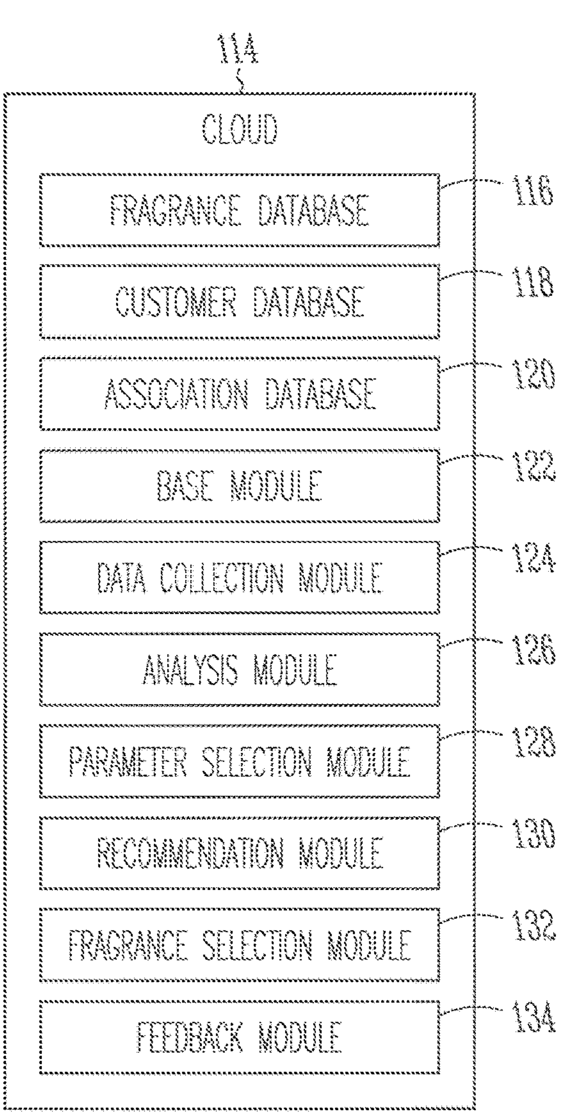
FIG. 1

| ID | BRAND | NAME |
|---|---|---|
| 11 | BURBERRY | HER EAU DE PARFUM |
| 99 | BURBERRY | MY BURBERRY EAU DE PARFUM |
| 9 | BURBERRY | MY BURBERRY BLUSH EAU DE PARFUM |
| 3 | BURBERRY | MR BURBERRY EAU DE TOILETTE |
| 24 | BURBERRY | MR BURBERRY INDIGO EAU DE TOILETTE |
| 173 | BURBERRY | BRIT FOR HER EAU DE PARFUM |
| 174 | BURBERRY | BRIT FOR HER EAU DE TOILETTE |
| 175 | BURBERRY | BRIT FOR HIM EAU DE TOILETTE |
| 184 | BURBERRY | MY BURBERRY EAU DE TOILETTE |

FIG. 2

| CUST. ID | GENDER | HOBBY | PERSONALITY | FRAGRANCE PREF. | PURCHASED | FEEDBACK (0-10) |
|---|---|---|---|---|---|---|
| 8812 | MALE | HIKING | CONFIDENT | WOODSY | NONE | N/A |
| 27046 | FEMALE | KAYAKING | ADVENTUROUS | REFRESHING | HER EAU DE PARFUM | 8 |
| 4456 | FEMALE | SEWING | RELAXED | FLORAL | BRID FOR HER EAU DE PARFUM | 5 |
| 11551 | FEMALE | STAMP COLLECTING | BOLD | CITRUS | NONE | N/A |
| 49178 | MALE | CYCLING | SPARKLING | NONE | NONE | N/A |
| 31732 | FEMALE | WOODWORKING | SEDUCTIVE | CITRUS | HER EAU DE PARFUM | 7 |
| 37469 | FEMALE | RUNNING | ADDITCTIVE | FRUITY | MY BURBERRY EAU DE TOILETTE | 9 |

FIG. 3

| FRAGRANCE | CUSTOMER CHARACTERISTIC | CORRELATION COEFFICIENT |
|---|---|---|
| HER EAU DE PARFUM | GENDER – MALE | 0.16 |
| HER EAU DE PARFUM | GENDER – FEMALE | 0.75 |
| HER EAU DE PARFUM | HOBBY – HIKING | 0.07 |
| HER EAU DE PARFUM | HOBBY – KAYAKING | 0.73 |
| HER EAU DE PARFUM | PERSONALITY – RELAXED | 0.85 |
| HER EAU DE PARFUM | PERSONALITY – ADDICTIVE | 0.93 |
| HER EAU DE PARFUM | FRAGRANCE PREF. – FRUITY | 0.84 |

FIG. 4

FRAGRANCE FINDER - OUR STARTING POINTS

Fragrance as part of an overall beauty and style proposition

Occasions

When looking for fragrance (online/ in-store)

When trying make-up or fashion (VTO)

When shopping for fashion (online)

When gifting someone (online)

FRAGRANCE FINDER - OVERARCHING PRINCIPLES

| EXPERIENCE | SERVICE | CONTENT | PRODUCT |
| --- | --- | --- | --- |
| **An online fragrance consultation** that provides personalized fragrance recommendations to everyone's real to desired self - bringing together personal narrative, olfactive and sensorial triggers, fashion and style expressions. | A gifting module to couple with retailer giftcard, such as a module to play as a retailer giftcard animation **making online fragrance consultation a service that comes with a giftcard or a service and you can gift someone** | **Consultation Starters** ("describe yourself ", "tell me who you want to be") <br> **Refinement Triggers** (Fragrance families and sensorial evocative content, Fashion and Lifestyle triggers) | **Breakthrough fragrance mapping** across a variety of attributes, from olfactive to storytelling, correlating to personality traits and subtraits, style and fashion. |

FIG. 13

FRAGRANCE FINDER: ONLINE FRAGRANCE CONSULTATION - BUILDING A A BREAKTHROUGH CONSUMER X PRODUCT MAPPING

| CONSUMER PROFILES | BRAND ARCHETYPES | FRAGRANCE USAGE & ATTITUDE | EDUCATION SCENT PERSONALITIES | DATA SCIENCE ITERATIONS |
| --- | --- | --- | --- | --- |
| Enriched consumer profiles across a variety of psychometrics, style and lifestyle, personality traits and sub-traits parameters | Enriched Luxury Fragrance Marketing brand/pillar archetypes - including digital/ social language and expressions | Existing Luxury CMI U&A studies exploring fragrance usage and attitudes against key demographics and psychometrics | Existing Luxury Fragrance Education database, which includes 3 "scent personality" keywords per fragrance | Previous data science iterations exploring links between personality types and fragrance preferences |

Luxury portfolio of fragrances (bestsellers, icons and flankers) to enable
Mapping across a variety of fragrance attributes and personality traits/profiles.

FIG. 18

APPENDIX I - LUXURY EDUCATION DATABASE:
3 KEYWORDS (SCENT PERSONALITY)

| | BRAND | COLLECTION | SOUS-COLLECTION | NAME | KEY WORDS 1 (SCENT PERSONALITY) | KEY WORDS 2 (SCENT PERSONALITY) | KEY WORDS 3 (SCENT PERSONALITY) |
|---|---|---|---|---|---|---|---|
| 11 | BURBERRY | | | Her Eau de Parfum | Adventurous | Spirted | Bold |
| 99 | BURBERRY | | | My Burberry Eau de Parfum | Refined | Confident | Iconic |
| 9 | BURBERRY | | | My Burberry Blush Eau de Parfum | Sparkling | Joyful | Playful |
| 3 | BURBERRY | | | Mr Burberry Eau de Toilette | Vibrant | Contemporary | Elegant |
| 24 | BURBERRY | | | My Burberry Indigo Eau de Toilette | Fresh | Energetic | Relaxed |
| 173 | BURBERRY | | | Brit For Her Eau de Parfum | Addictive | Seductive | Magnetic |
| 174 | BURBERRY | | | Brit For Her Eau de Toilette | Addictive | Seductive | Magnetic |
| 175 | BURBERRY | | | Brit For Him Eau de Toilette | Warm | Bold | Enveloping |
| 184 | BURBERRY | | | Mr Burberry Eau de Toilette | Fresh | Subtle | Delicate |

FIG. 19

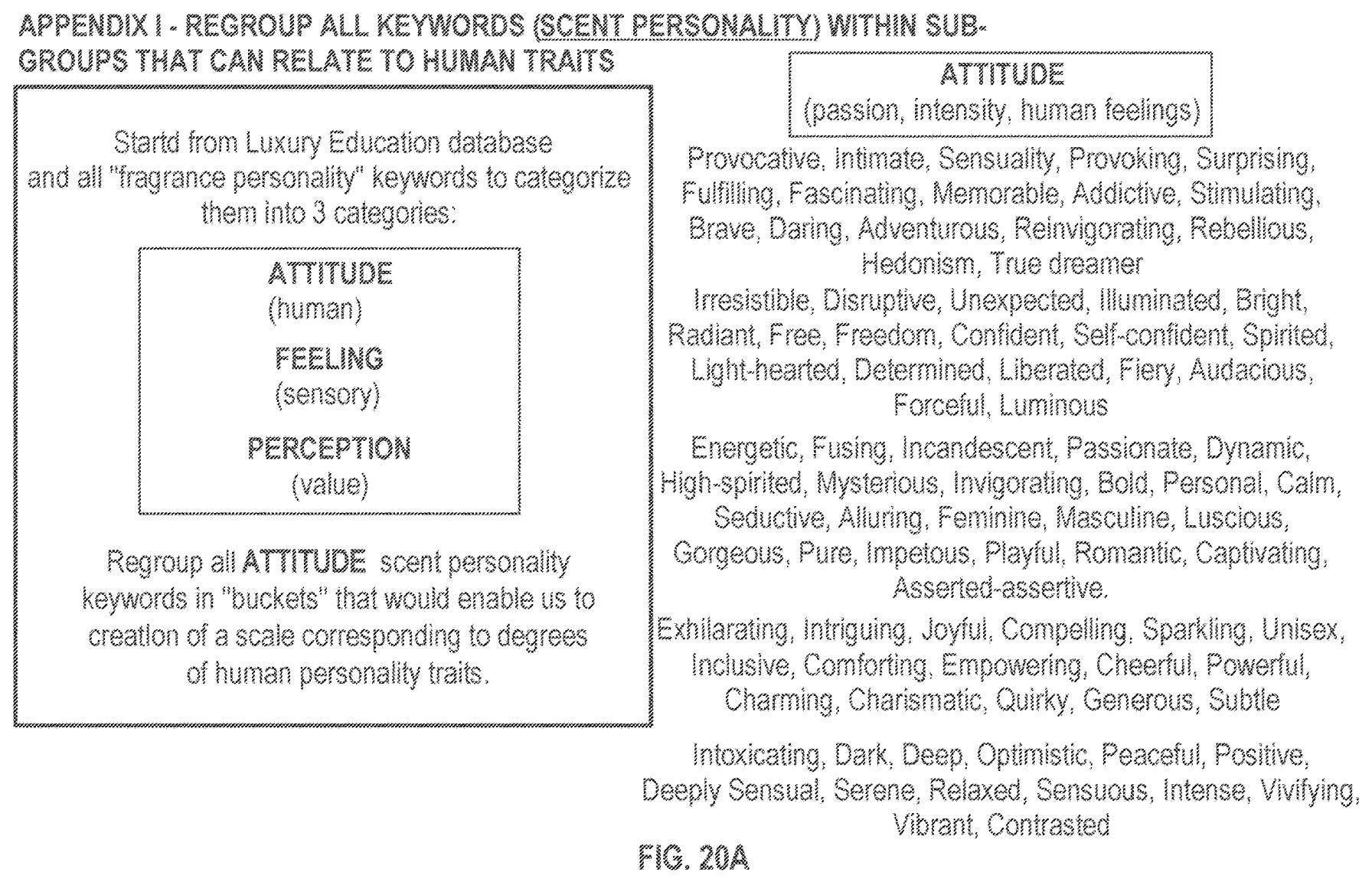

APPENDIX I - REGROUP ALL KEYWORDS (SCENT PERSONALITY) WITHIN SUB-GROUPS THAT CAN RELATE TO HUMAN TRAITS

Startd from Luxury Education database and all "fragrance personality" keywords to categorize them into 3 categories:

ATTITUDE
(human)

FEELING
(sensory)

PERCEPTION
(value)

Regroup all ATTITUDE scent personality keywords in "buckets" that would enable us to creation of a scale corresponding to degrees of human personality traits.

ATTITUDE
(passion, intensity, human feelings)

Provocative, Intimate, Sensuality, Provoking, Surprising, Fulfilling, Fascinating, Memorable, Addictive, Stimulating, Brave, Daring, Adventurous, Reinvigorating, Rebellious, Hedonism, True dreamer Irresistible, Disruptive, Unexpected, Illuminated, Bright, Radiant, Free, Freedom, Confident, Self-confident, Spirited, Light-hearted, Determined, Liberated, Fiery, Audacious, Forceful, Luminous Energetic, Fusing, Incandescent, Passionate, Dynamic, High-spirited, Mysterious, Invigorating, Bold, Personal, Calm, Seductive, Alluring, Feminine, Masculine, Luscious, Gorgeous, Pure, Impetous, Playful, Romantic, Captivating, Asserted-assertive.

Exhilarating, Intriguing, Joyful, Compelling, Sparkling, Unisex, Inclusive, Comforting, Empowering, Cheerful, Powerful, Charming, Charismatic, Quirky, Generous, Subtle Intoxicating, Dark, Deep, Optimistic, Peaceful, Positive, Deeply Sensual, Serene, Relaxed, Sensuous, Intense, Vivifying, Vibrant, Contrasted

FIG. 20A

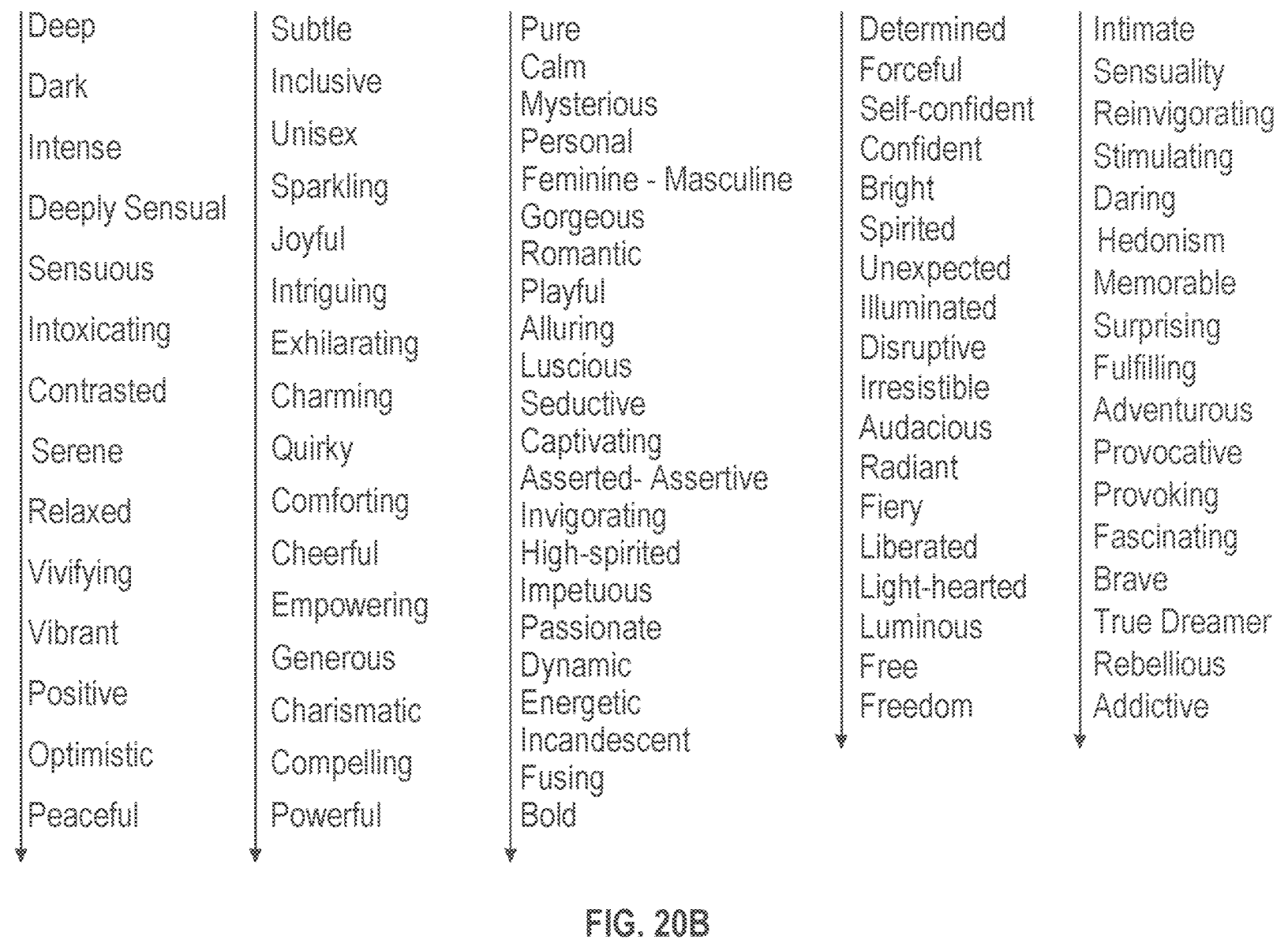

Deep
Dark
Intense
Deeply Sensual
Sensuous
Intoxicating
Contrasted
Serene
Relaxed
Vivifying
Vibrant
Positive
Optimistic
Peaceful Subtle
Inclusive
Unisex
Sparkling
Joyful
Intriguing
Exhilarating
Charming
Quirky
Comforting
Cheerful
Empowering
Generous
Charismatic
Compelling
Powerful Pure
Calm
Mysterious
Personal
Feminine - Masculine
Gorgeous
Romantic
Playful
Alluring
Luscious
Seductive
Captivating
Asserted- Assertive
Invigorating
High-spirited
Impetuous
Passionate
Dynamic
Energetic
Incandescent
Fusing
Bold Determined
Forceful
Self-confident
Confident
Bright
Spirited
Unexpected
Illuminated
Disruptive
Irresistible
Audacious
Radiant
Fiery
Liberated
Light-hearted
Luminous
Free
Freedom Intimate
Sensuality
Reinvigorating
Stimulating
Daring
Hedonism
Memorable
Surprising
Fulfilling
Adventurous
Provocative
Provoking
Fascinating
Brave
True Dreamer
Rebellious
Addictive

FIG. 20B

FIG. 20C

FEELING
(tactile, taste, nature)
Fiery
Cool
Ultra-fresh
Fresh
Warm
Exotic
Clean
Woody
Floral
Blooming
Refreshing
Lively
Revitalizing
Energizing
Mineral
Solar
Cooling
Oceanic
Green
Watery
Musky
Natural
Organic
Resinous
Spicy
Smoky
Crisp
Fruity
Aromatic
Sweet
Honeyed
Citrusy
Juicy
Gourmand
Delicious
Zesty
Delicate
Magnetic
Enveloping
Powdery
Velvety
Textured
Smooth
Soft
Tender
Caressing
Creamy
Wet

PERCEPTION
(time, luxury)

Timeless
Memorable
Contemporary
Modern
Classic
Vintage
Endless
Nostalgic
Sophisticated
Refined
Elegant
Distinctive
Exclusive
Majestic
Noble
Unique
Iconic
Royal
Ethereal
Golden
Original
Luxurious
Lush
Dazzling
Rich
Authentic
Opulent
Precious
Fascinating
Emblematic
Voluptuous
Mesmerizing
Delightful
Glamour
Enchanting
Graceful
Mysterious
Effortless
Universal APPENDIX I - REGROUP ALL KEYWORDS (SCENT PERSONALITY) WITHIN SUB-GROUPS THAT CAN RELATE TO HUMAN TRAITS

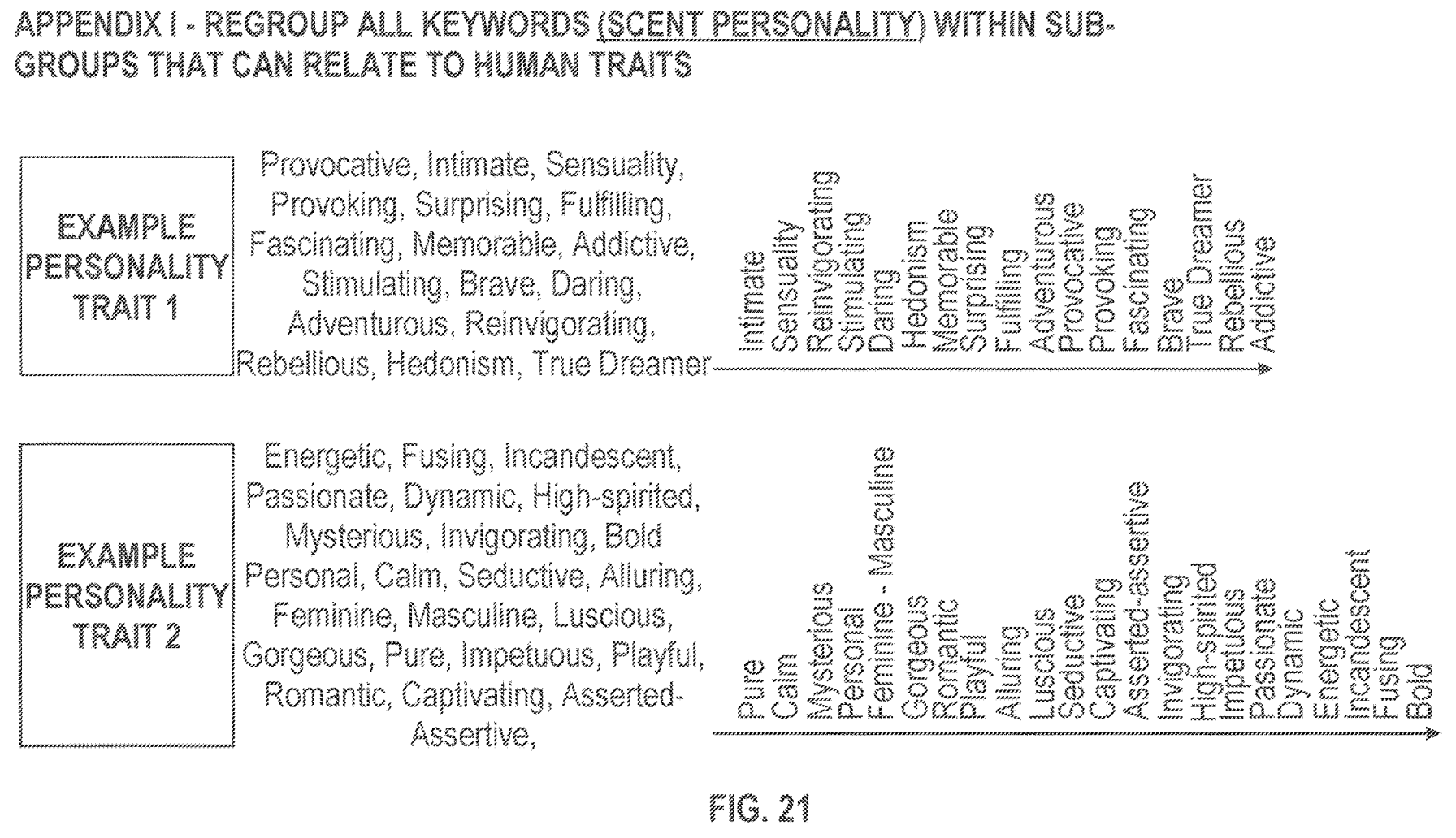

EXAMPLE PERSONALITY TRAIT 1

Provocative, Intimate, Sensuality, Provoking, Surprising, Fulfilling, Fascinating, Memorable, Addictive, Stimulating, Brave, Daring, Adventurous, Reinvigorating, Rebellious, Hedonism, True Dreamer Intimate
Sensuality
Reinvigorating
Stimulating
Daring
Hedonism
Memorable
Surprising
Fulfilling
Adventurous
Provocative
Provoking
Fascinating
Brave
True Dreamer
Rebellious
Addictive

EXAMPLE PERSONALITY TRAIT 2

Energetic, Fusing, Incandescent, Passionate, Dynamic, High-spirited, Mysterious, Invigorating, Bold Personal, Calm, Seductive, Alluring, Feminine, Masculine, Luscious, Gorgeous, Pure, Impetuous, Playful, Romantic, Captivating, Asserted-Assertive, Pure
Calm
Mysterious
Personal
Feminine - Masculine
Gorgeous
Romantic
Playful
Alluring
Luscious
Seductive
Captivating
Asserted-assertive
Invigorating
High-spirited
Impetuous
Passionate
Dynamic
Energetic
Incandescent
Fusing
Bold

FIG. 21

AI PERSONAL FRAGRANCE CONSULTATION AND FRAGRANCE SELECTION/RECOMMENDATION

CROSS-REFERENCE TO RELATED APPLICATION

This application is a U.S. National Stage Filing under 35 U.S.C. 371 from International Application No. PCT/US2023/062648, filed on 15 Feb. 2023, and published as WO 2023/159056 on 24 Aug. 2023, which application claims the benefit of priority to U.S. Application Ser. No. 63/310,493, filed Feb. 15, 2022, and U.S. Application Ser. No. 63/385,082, filed Nov. 28, 2022, which are incorporated by reference herein in their entirety.

FIELD OF THE DISCLOSURE

The present disclosure is generally related to fragrances, particularly the recommendation of one or more fragrances.

BACKGROUND

How scents are perceived and associated is highly subjective and varies widely between individuals. This makes it uniquely difficult to recommend a fragrance for products such as perfumes or where scents are added.

Further complicating the subjective nature of fragrance preference is that it may also be affected by the mental or emotional state of each individual in addition to their own memories and experiences. Scent has long been established as having a strong associative link to memories.

With a wide range of variables and scents, what is needed is a method of identifying the most probable predictors for fragrance preferences and further the ability to produce a recommendation based upon the identified predictors.

The difficulty of matching fragrances to an individual's preferences makes marketing products where fragrances are used difficult. The ability to match fragrances to user preferences can aid in creating new or personalized formulations of fragrances, marketing of scented products, and may also prove useful in some therapeutic applications.

DESCRIPTIONS OF THE DRAWINGS

FIG. 1: Illustrates a system for making a fragrance recommendation, according to an embodiment.

FIG. 2: Illustrates a fragrance database, according to an embodiment.

FIG. 3: Illustrates a customer database, according to an embodiment.

FIG. 4: Illustrates an association database, according to an embodiment.

FIG. 5: Illustrates a base module, according to an embodiment.

FIG. 6: Illustrates a data collection module, according to an embodiment.

FIG. 7: Illustrates an analysis module, according to an embodiment.

FIG. 8: Illustrates a parameter selection module, according to an embodiment.

FIG. 9: Illustrates a recommendation module, according to an embodiment.

FIG. 10: Illustrates a fragrance selection module, according to an embodiment.

FIG. 11: Illustrates a feedback module, according to an embodiment.

FIG. 12: Illustrates fragrance as a beauty and style proposition, according to an embodiment.

FIG. 13: Illustrates components of fragrance recommendation, according to an embodiment.

FIG. 14: Illustrates an example of a workflow for making a fragrance recommendation, according to an embodiment.

FIG. 15: Illustrates an example of a gifting workflow for making a fragrance recommendation, according to an embodiment.

FIG. 16: Illustrates an example of a personality link between conversation starters and refinement triggers, according to an embodiment.

FIG. 17: Illustrates examples of refinement triggers, according to an embodiment.

FIG. 18: Illustrates an example of customer to product mapping, according to an embodiment.

FIG. 19: Illustrates an example of a scent to personality database, according to an embodiment.

FIGS. 20A, 20B, and 20C: Illustrate classification of personality traits, according to an embodiment.

FIG. 21: Illustrates an example of keyword grouping, according to an embodiment.

DETAILED DESCRIPTION

Figures 5, 6:
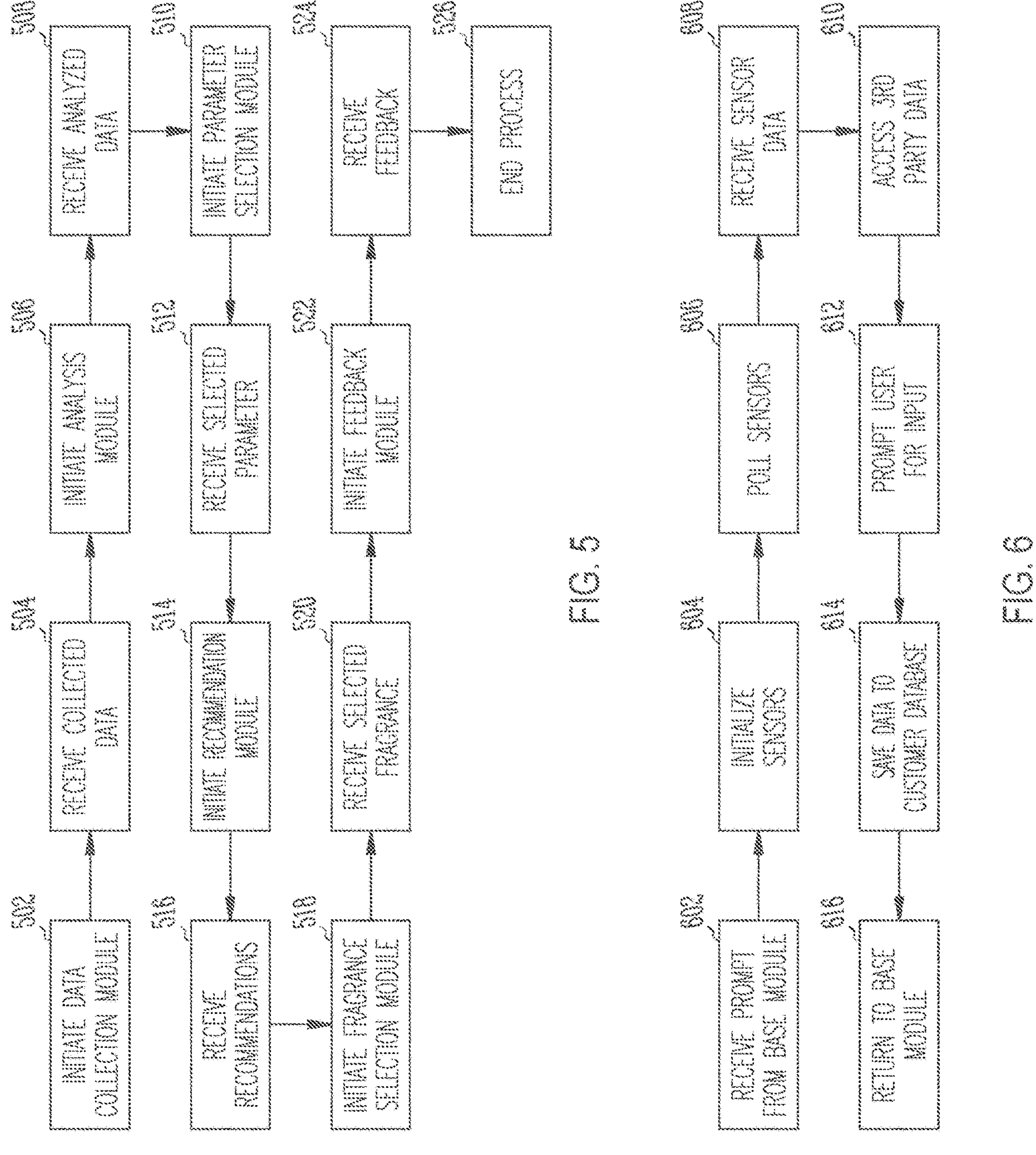

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Provided herein is an artificial intelligence tool to help consumers to select one or more fragrances (aka perfumes) that are suitable to them. For example, fragrance recommendations based on AI diagnostic of personality and reaction to sensory (olfactive families), style (fashion) and lifestyle (social; emotions; projections; preference; occasion/event) stimuli, and optionally combined with analysis of face attributes (including, but not limited to eyebrow shape (e.g., straight, hard-angled, soft-angled, rounded, dense, average thickness, sparse, far-apart, close gap in between, thin, normal thickness, short, or normal length), eye shape (e.g., wide-set, close-set, average-set, big, small, average size, upturned, downturned, average angle, almond, round, narrow, mono lid, double lid, hooded, deep-set, amber, brown, blue, gray, green, other color, or eye color), nose shape (e.g., broad, narrow, average width, long, short, or average length), cheekbones (e.g., flat, high, low, or round), face shape (e.g., Oblong, square, heart, round, triangle, diamond, or oval) and/or lip shape (e.g., heavy lower lip, heavy upper lip, thin, full, wide, narrow, round, bow, downturned, average, or lip color)) which can be correlated to traits (including, but not limited to extroversion (e.g., positive emotions, excitement-seeking, activity level, assertiveness, gregariousness, and warmth), agreeableness (e.g., trust, earnestness, altruism, cooperation-compliance, modesty, and sympathy-compassion), openness (e.g., fantasy, aesthetic interest, emotional orientation, experimentation, intellectualism, and diversity-tolerance), conscientiousness (e.g., self-assurance, orderliness, dutifulness, achievement-striving, self-discipline, and prudence) and neuroticism (e.g., Anxiety, irritability, immoderation, self-consciousness, depressive tendencies, and vulnerability)) and sub-traits (altogether these attributes contribute to fragrance mapping for an individual), that then can used to further refine the fragrance recommendation(s) for the consumer.

As can be seen from the drawings and appendices, keywords from consumer consultation match to categories that lead to a scent personality and then to a fragrance recommendation(s)/mapping.

One aspect provides an online fragrance consultation that provides personalized fragrance recommendations to everyone's real to desired self, bringing together personal narrative, olfactive and sensorial triggers, fashion and style expressions. In one aspect, the language from the consultation provides transcending perfumery language and conventions to help luxury fragrance consumers find what they are looking for, no matter how they express it and whatever their culture, gender or dreams. In another aspect, the online consultation results in a (retailer) gifting card or program, providing a gifter with the opportunity to offer an online fragrance consultation with a gift card.

This is a system for making a fragrance recommendation. This system comprises an electronic device 102 is a computing device which and which may comprise any of a mobile device, phone, tablet, laptop computer, desktop computer, kiosk, etc. The electronic device 102 may comprise a general-purpose computational device or a purpose built, proprietary computational device such as a kiosk or terminal which may be present in a retail location. The electronic device 102 may comprise at least one of sensors 104, a camera 106, a microphone 108, or an input device 110. The electronic device 102 may comprise a communication interface 112 configured to communicate with the internet or a cloud 114. The communication interface 112 may be connected to one or more electronic devices 102 such as wearable mobile devices including smart watches or wearable sensors 104. The communication interface 112 may also be connected to one or more cameras 106 or microphones 108. For the purpose of this invention, any such sensors 104, cameras 106, microphones 108 or input devices 110 which may be connected to the electronic device 102 via a communication interface 112 will be referred to as a component of the electronic device 102, however any such component may alternatively be one or more separate remote devices connected to the electronic device 102 via a communication interface. A sensor 104 is a detection or measurement device configured to collect data. Sensors 104 typically measure and quantify analog inputs and convert them to digital data though some may natively collect and monitor digital data. Sensors 104 may be any of position sensors (accelerometers, global positioning system, etc.), pressure sensors (manometers, barometers, etc.), temperature sensors (bolometers, thermocouples, thermometers, etc.), force sensors (force transducers), vibration sensors, piezo sensors, fluid property sensors, humidity sensors, strain gauges, photo optic sensors, flow switches, level switches and may further require contact with the item, substance, or material they are measuring or may not require contact. Similarly, some sensors may measure rotary movement, versus linear movement. Non-contacting sensors may additionally comprise hall effect sensors, capacitive sensors, eddy current sensors, ultrasonic sensors, laser sensors or proximity sensors. Sensors 104 may additionally comprise consumable or catalytic chemical reactions including assays. Additional embodiments may include biometric monitoring sensors such as a pulse oximeter, galvanic skin response sensor, blood pressure, electrocardiogram (EKG), etc. A camera 106 is an imaging sensor or array of imaging sensors which take measurements, typically of reflected light, which are then used to recreate and image from the measurements on a display. Each measurement is used to populate values to a pixel or subpixel. Multiple subpixels may create a complete pixel and an array of pixels creates an image. In some embodiments, a plurality of sensor measurements may be used to populate a single pixel or subpixel. The plurality of sensor measurements may be taken from one imaging sensor over a period of time or from multiple imaging sensors taken simultaneously or also over a period of time. The multiple measurements may be averaged together or subjected to a smoothing algorithm to determine a pixel or subpixel values. Each pixel or subpixel value may be determined independently or may be determined via image processing of a part or the whole image, comprised of a plurality of measurements in an array to which one or more algorithms may be applied such as smoothing, edge detection, etc. A microphone 108 is an audio input device which detects sound waves and converts the analog signal into digital data. The microphone 108 may be integrated into an electronic device 102, a wearable device, or be a standalone microphone interfaced with an electronic device wirelessly or via a cable. Examples of a microphone include condenser microphones, dynamic microphones, electret microphones, etc. The microphone 108 may comprise a single audio pickup capsule or may comprise a plurality of audio pickup capsules. A microphone may be integrated into an electronic device 102 or connected via a cable or wirelessly via a communication interface 112. An input device 110 is any device for capturing input from a user such as a keyboard, keypad, mouse, remote control, joystick, or any other array of switches, dials, etc. arranged to receive input from a user. An input device 110 may additionally be configured to capture gestures such as via a wearable device worn by the user or an image capture system for capturing and analyzing images and/or video to detect gestures made by a user. An input device 110 may additionally comprise a touch screen interface, such as a capacitive, resistive, or pressure detecting surface which may or may not be overlayed upon or beneath a screen capable of displaying content to a user. An input device 110 may also comprise a stylus. A communication interface 112 provides a connection between one or more electronic devices 102 or components. A communication interface 112 may have a physical interface to accept a cable connector such as an ethernet cable, optical cable, USB cable, etc. or may provide for a wireless connection. To provide a wireless connection, a communication interface 112 will include an antenna to send and/or receive data via electromagnetic waves. Wireless connections may be established using any communication protocol such as Wi-Fi, Bluetooth, infrared (IR), cellular (3G, 4G, 5G, LTE, etc.), near field communication (NFC), radio frequency identification (RFID), global positioning system (GPS), etc. In some embodiments, a communication interface 112 may utilize light to establish a physical connection, such as using fiberoptic cables or wirelessly via one or more lasers, visible light communication, etc. A cloud 114 is a network of distributed computational and data storage resources. A cloud 114 may be a public cloud, such as accessible via the internet, or may be a private cloud, which may be isolated from access via the internet. Similarly, a cloud 114 may be widely accessible or access may be restricted via encryption, authentication, etc. In some embodiments, a cloud 114 may be maintained by a third party, where resources are provisioned for one or more users and/or organizations. A fragrance database 116 stores data related to the name, descriptions, characteristics, ingredients, and chemical makeup of a plurality of fragrances or compounds for adding scents and/or flavors to products such as perfumes, colognes, candles, air fresheners, shampoo, bodywash, deodorants, personal care products, detergents, etc. The data may additionally include manufacturer and information related to the manufacture of the fragrances. The data may be populated by one or more manufacturers, vendors, such as via a connected third-party database via the cloud 114. The customer database 118 stores data about one or more customers. The data may comprise characteristics which describe the user universally, such as applicable at all times, or conditionally, such as only applicable sometimes under certain conditions. Universal characteristics may comprise a customer's personality, genetic information, allergies, customers' stated preferences unless indicated as conditional, etc. Conditional characteristics may comprise a customer's mood, an occasion, location or environment, etc. The customer database 118 is populated by the data collection module 124 and the feedback module 134 and may additionally be populated by one or more proprietary or third-party database and one or more application programming interfaces (APIs). In some embodiments, customer data may be stored in accordance with a privacy and/or customer data retention policy and/or in compliance with regulations such as the General Data Protection Regulation (GDPR). The association database 120 stores data relating to the relationship between one or more customer characteristics and one or more fragrances. The association data being indicative of the one or more customer characteristics likelihood of predicting one or more customers' preferences for one or more fragrances. The association database 120 is populated by the analysis module 126 and is used by the parameter selection module 128 and the recommendation module 130. The base module 122 initiates the data collection module 124 which collects data from at least one data source including any of a sensor, camera, microphone, input device, third party database, proprietary database, survey, etc. and saves the collected data to the customer database 118. The base module 122 receives the collected data from the data collection module 124 and initiates the analysis module 126. The analysis module 126 uses the collected data and data stored in the customer database 118 and the fragrance database 116 to identify one or more associations, or pairing of customer characteristics and fragrances, which are saved to the association database 120. The base module 122 receives the associations from the analysis module 126 and initiates the parameter selection module 128. The parameter selection module 128 evaluates each association to determine whether the associations are strong predictors of a preference for one or more fragrances and the parameter selections are saved to the association database 118. The base module 122 receives the selected parameters from the parameter selection module 128 and initiates the recommendation module 130 which creates and/or trains a recommendation model which is used to generate one or more fragrance recommendations. The base module 122 receives the one or more fragrance recommendations from the recommendation module 130 and initiates the fragrance selection module 132. The fragrance selection module selects one or more fragrances from the recommended fragrances identified by the recommendation module 130. The base module 122 receives the selected fragrance(s) from the fragrance selection module 132 and initiates the feedback module 134. The feedback module 134 receives feedback from one or more customers and saves the feedback to the customer database 118. The base module 122 receives the customer feedback from the feedback module 134 and ends the recommendation process. The data collection module 124 collects data from at least one source comprising any input device 110, such as cameras, sensors, third party or proprietary databases, etc. The data collection module 124 initializes the input devices 110 and receives data from the devices which is then saved to the customer database 118. The analysis module 126 receives data from the customer database 118 and the fragrance database 116. The analysis module 126 selects customer characteristic data from the customer database 118 and fragrance data from the fragrance database 116 and identifies associations for pairings of customer characteristics and fragrance. In some embodiments, the associations are quantifiable, whereas in other embodiments, the associations are subjective or may be made by a human screener. The associations are saved to the association database 120 and the process is completed for all combinations of customer characteristics and fragrances. The parameter selection module 128 receives data from the fragrance database 116 and the association database 120 and the association data is assessed for the ability to predict a preference for each fragrance, such as by comparing a quantified correlation coefficient to a threshold value and selecting the correlation as a parameter. Alternatively, the associations with the highest correlation coefficients may be selected as parameters. The parameters will be used to create a recommendation model which will be used to select one or more fragrances to recommend to one or more customers. The recommendation module 130 receives the selected parameters determined by the parameter selection module 128, and data from the customer database 118, to train a recommendation model. In an embodiment, the recommendation model may be a machine learning model. In alternate embodiments, the recommendation model may comprise a lookup table, decision tree, etc. The recommendation model is then used to generate recommendations from the plurality of available fragrances stored in the fragrance database 116, which may comprise a preference score representing the customer's probability of responding positively to a fragrance. The recommendations may comprise a set or combination of fragrances, a class of fragrances, etc. The fragrance selection module 132 receives a plurality of recommendations generated by the recommendation module 130 and additionally data from the fragrance database 116 and the customer database 118 which is used to select one or more fragrances. Additionally, customer characteristics, preferences, or other weightings may be considered when selecting one or more fragrances. The feedback module 134 receives the selected fragrances and sends a feedback request to the customer. The feedback request may be included with a sample of the recommended fragrances. Alternatively, the feedback request may comprise a digital survey request. The feedback module 134 further receives feedback from one or more customers which may comprise the completion of a survey or may comprise behavioral cues such as purchasing products containing one or more of the recommended fragrances, returning a product containing a fragrance, recommending a fragrance or product containing a fragrance to a social connection, or facial analysis of the customer's reaction when using or encountering a fragrance or a product containing a fragrance.

Functioning of the "Fragrance Database" will now be explained with reference to FIG. 2. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the fragrance database 116. The fragrance database 116 stores data related to one or more fragrances. The data at least comprising a fragrance name and a unique identifier or ID. The fragrance database 116 may additionally comprise descriptions, characteristics, ingredients, and the chemical makeup of a plurality of fragrances or compounds for adding scents and/or flavors to products such as perfumes, colognes, candles, air fresheners, shampoo, bodywash, deodorants, personal care products, detergents, etc. The data may additionally include information about the manufacturer, brand, and vendor information and information related to the manufacture of the fragrances including manufacturing process steps. The data in the fragrance database 116 may be populated by one or more fragrance manufacturers, vendors, etc., and is utilized by the analysis module 126, the parameter selection module 128, the recommendation module 130, and the fragrance selection module 132.

Functioning of the "Customer Database" will now be explained with reference to FIG. 3. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the customer database 118. The customer database 118 stores data about one or more customers. The data may comprise identifiable information, such as name, phone number, email address, home address, etc., and may comprise characteristics which describe the user. Customer data, in particular personal identifiable information, shall be stored in compliance with privacy and customer data retention policies in addition to regulations such as the General Data Protection Regulation (GDPR). Such policies and regulations may require consent from customers prior to data being captured, stored, or transmitted to a server for analysis. In some embodiments, data may be collected and stored locally on a customer's private device without obtaining permission, however such permission may still be required prior to analysis of the obtained data. Obtained data analyzed using a private device, including but not limited to the results of the analysis, may not be transmitted external to the device without receiving consent from the customer. In some embodiments, consent may be implied, such that the user is presented with a message that continuing to use the device and/or program is considered consent to use their personal information, whereas in other embodiments consent is explicit, requiring the customer to make a selection confirming, or denying consent. Examples of characteristics may include gender, hobbies, personality traits, fragrance preferences, items purchased, feedback related to purchased products, etc. Data may additionally include information such as genetic information, allergies, non-fragrance preferences, mood, personality, reactions to stimuli, occasions of interest, locations, environments, etc. Some customer characteristics may such as personality, mood, reactions, etc. may be determined based upon analysis of other customer characteristics such as facial features, tone of voice, etc. These features may be used as customer characteristics directly and/or may be used to derive an intermediary customer characteristic such as personality, mood, reactions, etc. The customer database 118 is populated by the data collection module 124 and the feedback module 134 and may additionally be populated by one or more proprietary or third-party databases and/or application programming interfaces (APIs). Examples of connected third-party data sources may include social media networks, vendor websites, search engine, web tracking and advertisement services, etc. The customer database 118 is utilized by the analysis module 126, the recommendation module 128, and the fragrance selection module 132. In some embodiments, the customer database 118 may additionally be utilized by the feedback module 134 to determine where to send feedback requests such as customer satisfaction surveys and additional promotions.

Functioning of the "Association Database" will now be explained with reference to FIG. 4. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the association database 120. The association database 120 stores data relating to the relationship between one or more customer characteristics and one or more fragrances. The association data indicates the degree to which the one or more customer characteristics are associated with the one or more fragrances such as indicated by a correlation coefficient. Other descriptors of an association may be descriptive rather than quantitative, such as high, medium, or low. Other examples may include unlikely, somewhat unlikely, indifferent, somewhat likely, or likely to have a predictive association such that the customer characteristics may indicate or be used to predict a preference for one or more fragrance. The association database 120 is generated by the analysis module 126 and is used by the parameter selection module 128.

Functioning of the "Base Module" will now be explained with reference to FIG. 5. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the base module 122. The process begins with initiating, at step 502, the data collection module 124. The data collection module 124 initializing sensors 104, cameras 106, microphones 108 and other input devices 110 and polling the initialized devices for data. The data collection module 124 additionally accessing third party data, such as from social media, and prompting the user to provide direct input via at least an input device 110. The data is saved to the customer database 118. Receiving, at step 504, the collected data from the data collection module 124. The data may be collected from any of one or more sensors 104, cameras 106, microphones 108, input devices 110, or third-party sources such as private or proprietary databases owned and maintained by social media companies. Initiating, at step 506, the analysis module 126. The analysis module 126 querying the customer database 118 and the fragrance database 116 and selecting a first fragrance and a first customer characteristic. Calculating correlations and/or identifying associations between the first fragrance and the first customer characteristic and saving the calculated correlations and/or identified associations to the association database 120. Further determining whether there are more customers and selecting a second customer characteristic if there are more customer characteristics available to analyze, otherwise determining whether there are more fragrances available. If there are more fragrances available, selecting a second fragrance to analyze. Receiving, at step 508, the analyzed data from the analysis module 126 comprising correlations and/or identified associations when all customer characteristic and fragrance combinations have been analyzed. The resulting data may be quantitative, such as correlation coefficients representing the likelihood of one or more customer characteristics being predictors for a preference for one or more fragrances or may be more generalized associations between customer characteristics and fragrances. Initiating, at step 510, the parameter selection module 128. The parameter selection module 128 querying the fragrance database 116 and the association database 120 and selecting a first fragrance and a first association such as by comparing a correlation coefficient with a threshold value. Alternatively, an association may be identified between a customer characteristic and a fragrance via methods which do not rely on statistical principals including subjective assessments. Associations may be evaluated for the strength of the association and may additionally consider the context of the association, such that the combination of multiple associations may increase the predictive relevance of the association. A correlation or association is selected as a parameter if the correlation coefficient is above a threshold value, or the association is found to be a sufficient predictor of a fragrance preference. If there are more associations, a second association is selected, otherwise if there are more fragrances, a second fragrance is selected. Receiving, at step 512, the selected parameters from the parameter selection module 128. The selected parameters comprising correlations and/or associations which represent pairings of customer characteristics and fragrances which have a high likelihood of accurately predicting a customer's preference for one or more fragrances. Initiating, at step 514, the recommendation module 130. The recommendation module 130 querying the customer database 118 and the fragrance database 116 for data related to the selected parameters and using the data, comprising related customer characteristics and fragrances to train a recommendation model. In some embodiments, the recommendation model may be a lookup table or a decision tree. The recommendation model being further used to generate one or more fragrance recommendations. Receiving, at step 516, one or more fragrance recommendations from the recommendation module 130. The recommendations may comprise one or more fragrances, fragrance families, or groups of fragrances sharing common characteristics. Initiating, at step 518, the fragrance selection module 132. The fragrance selection module 132 querying the fragrance database 116 and the customer database 118 for recommended fragrance data and additional customer data such as customer input and feedback and selecting one or more fragrances from the recommended fragrances. Receiving, at step 520, one or more selected fragrances from the fragrance selection module 132. Initiating, at step 522, the feedback module 134. The feedback module 134 receiving one or more selected fragrances and optionally requesting feedback from one or more customers. Receiving customer feedback via direct or indirect methods, such as by providing surveys or monitoring sales activity and saving the customer feedback to the customer database 118. Receiving, at step 524, customer feedback from the feedback module 134. The customer feedback comprising data which explicitly or implicitly indicates one or more preferences for one or more fragrances. Ending, at step 526, the fragrance recommendation process.

Functioning of the "Data Collection Module" will now be explained with reference to FIG. 6. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the data collection module 124. The process begins with receiving, at step 602, a prompt from the base module 122 to begin data collection. The prompt may be automated or a manual action to begin collecting data from one or more customers. The data collection may be prompted by customer actions, such as registration at a website, purchase of a product containing a fragrance, etc. Initializing, at step 604, one or more sensors 104, to be used in data collection. Initializing including the powering on of the sensor 104 devices and may additionally comprise a handshake, where a signal is sent to the sensors 104 and a response is received to confirm that the sensor 104 has powered on and is ready to collect data. Sensors may additionally refer to cameras 106, microphones 108, or any other input device 110. In an embodiment, establishing a connection with the sensors 104 in a mobile phone including the phone's accelerometer, microphone(s), camera(s), etc. Polling, at step 606, the one or more sensors 104, cameras 106, microphones 108, input devices 110, etc. for data input. In an embodiment, an accelerometer may collect position and movement data from a customer. In a further embodiment, a microphone 108 may collect audio data containing the customer's voice which may later be analyzed to determine the customer's sentiment. Similarly, camera 106 data may be collected. Further embodiments may collect data from sensors 104 configured to detect and analyze the composition of volatile compounds to determine the scents present when collecting data about the customer. Similarly, the position data may be used to determine where in a store the customer is positioned and determine which scented products or fragrance samples the customer may be near while collecting data which can be used to measure the customer's reactions. In an embodiment, at least one camera 106 oriented towards a customer captures at least one image of the customer while the customer is presented with at least one fragrance such that the at least one image comprises a facial expression reacting to the at least one fragrance. In other embodiments, a fragrance is not present, however the customer may be prompted to make an expression following an instruction which is captured by the at least one camera 106. Such image data may later be used to identify a reaction, mood, or personality which may be evaluated as a potential predictor of a fragrance preference. In another embodiment, camera 106 captures image data of a customer in order to conduct facial feature analysis, such as shape, features and spacing, etc. that may be related to a set of personality characteristics and further used as a potential predictor of a fragrance preference. Similarly, one or more microphones 108 may be used to collect audio samples of the customer's voice upon which the audio can be processed, and the tone of the customer's voice analyzed for indications of reaction, mood, or personality which may be evaluated as a potential predictor of a fragrance preference. The customer may also submit data via one or more input devices 110 such as by following prompts and answering questions on a touch screen or entering data via a keyboard and/or mouse. Receiving, at step 608, sensor 104 data from the sensors 104. The sensor 104 data may be temporarily stored in the sensor 104 devices and transmitted to an electronic device 102 in batches or packets or may be streamed continuously. The method of data transfer may be dependent on network connectivity at the time of data collection such that data is stored on the local sensor 104 device while there is a poor or no network connection to the electronic device 102, internet, or cloud 114, and is then transmitted when the network connection is available. Likewise, when the network connection is available, the data may be streamed in real time. In an embodiment, the electronic device 102 having a reliable connection with at least one sensor 104, such as an accelerometer, and receiving data in real time. In an embodiment, image data is received in real time from at least one camera 106 oriented towards the customer's face, capturing facial expressions. A microphone 108 may additionally be used to collect the customer's voice. Accessing, at step 610, third party data from one or more third party data sources. third party data may comprise a connected device comprising a plurality of sensors 104, cameras 106, microphones 108, and input devices 110. third party data sources may additionally comprise databases owned and managed by a third party such as those managed by social media providers. In an embodiment, the data collection module 124 accessing social media data from Facebook and Twitter and determining the friends, followers, and people the customer is following and additionally collecting public posts made by the customer and by the customer's friends, followers, etc. which mention or tag the customer. The social media data may additionally comprise products and services that the customer has liked or otherwise expressed interest in. Third party data may also comprise sales and returns data from one or more vendors for fragrances as well as clothing, cosmetics, personal care products, etc. Third party data may further relate to location, geography, climate, weather, and calendar data, including from public and private calendars. In an embodiment, connecting to a retailer's database and confirming that a female customer with customer ID 27046 purchased Her Eau de Parfum. Prompting, at step 612, the user, or customer, for input. Prompts for input may comprise a text message, instructions on a kiosk, mobile device screen, website, etc. and the user input may be provided via an input device 110. User input may additionally or alternatively be provided by one or more sensors 104, cameras 106, microphones 108, etc. For example, a prompt may request that the customer read text aloud or dictate their response orally to be received via a microphone. In an alternate embodiment, the user may be provided images or fragrances and their reactions may be captured via one or more cameras 106. Further embodiments may comprise completion of a survey via a keyboard input device 110. A prompt for user input may additionally comprise a live video interaction between the customer and a video recording, or with a live person, or dynamically generated content, or using pre-recorded video feed. Saving, at step 614, the data collected by the data collection module 124 to the customer database 118. Returning, at step 616, to the base module 122.

Figure 7:
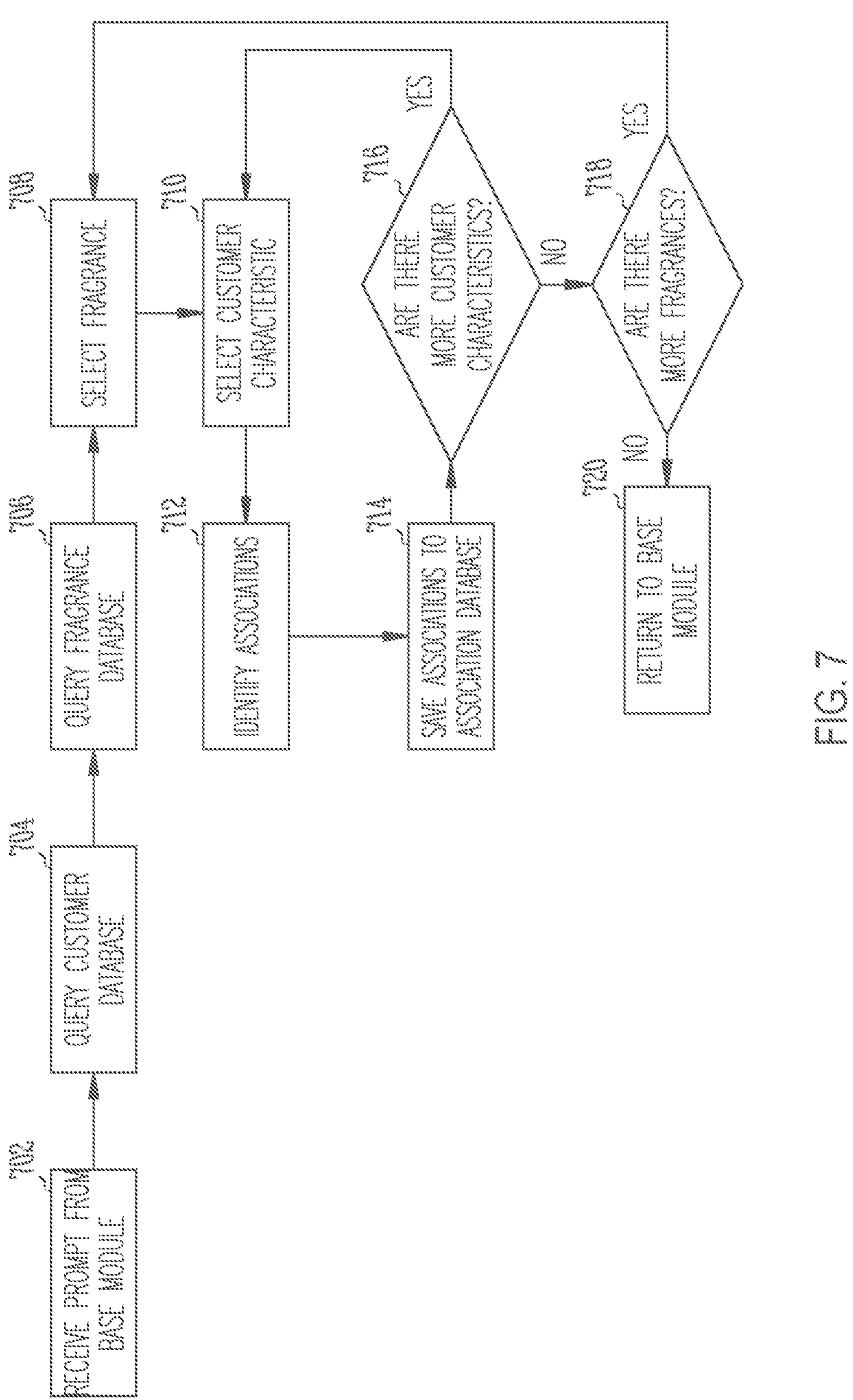

Functioning of the "Analysis Module" will now be explained with reference to FIG. 7. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the analysis module 126. The process begins with receiving, at step 702, a prompt from the base module 122. The prompt may contain customer data collected from the data collection module 124. The prompt may additionally include instructions such as to perform an analysis of all data, only newly collected data, or only data pertaining to a specific customer. Querying, at step 704, the customer database 118 for customer characteristic data from at least one customer. The data may additionally comprise customer feedback data such as a customer's fragrance preferences to include fragrances they liked, fragrances they did not like, and may additionally include quantifiable scoring, such as a customer describing a fragrance with an ID of 11 with a score of 7 out of 10. Examples of customer characteristic data may comprise images of a customer's face including when the customer is reacting to a particular fragrance. The data may comprise voice and or video recordings of the customer responding to prompts. Customer characteristics may additionally comprise hobbies, personality traits, their gender, location, places visited, purchase history, etc. Any data which could be used to describe a customer, their preferences, behaviors, etc. may be used as customer characteristics. The customer data may be aggregate data or may be for a single customer. Querying, at step 706, the fragrance database 116 for one or more fragrances. The fragrance data may include specific fragrances, but may also include their characteristics, ingredients, etc. such that analysis of customer characteristics paired with fragrances may alternatively be between fragrance characteristics and/or ingredients. This allows for more generalized comparisons and recommendations instead of only explicit comparisons. In some embodiments, both explicit and generalized data is used to allow the identification of a family of related or similar fragrances from which a recommendation may be selected for a customer. Selecting, at step 708, a fragrance, fragrance characteristic, or fragrance ingredient from the data retrieved from the fragrance database 116. In an embodiment, selecting the fragrance with ID 11, Her Eau de Parfum. Selecting, at step 710, a customer characteristic from the customer data retrieved from the customer database 118. In an embodiment, the customer characteristic is an image of the customer taken when the customer was sampling the fragrance with ID 11. The customer may have instead been sampling a different fragrance than the selected fragrance. The customer characteristic can alternatively be unrelated to fragrances, such as the user's personality, mood, favorite food, favorite activities, etc. In another embodiment, selecting an adventurous personality as a customer characteristic. In some embodiments, customer characteristics may comprise categories or groups of customers which may be characterized by one or more customer characteristics. For example, people with adventurous personalities, or a preference for fruity fragrances, or who like a particular activity such as hiking. Other groupings may relate to demographics, habits, musical preferences, clothing, hair or cosmetic style preferences, preferred reading genres, etc. In some embodiments, customer characteristics may comprise emotions, or a customer's emotional state. The customer's emotional state may be identified based upon facial expressions, gestures, tone of voice, message context or biometric information such as heart rate, blood pressure, galvanic skin response, EKG, etc. The emotional state may be identified using similar methods to personality via one or more algorithms including machine learning. Identifying, at step 712, an association between the selected customer characteristic and the selected fragrance. In an embodiment, an association is determined by calculating a correlation coefficient representing the probability of the selected customer characteristic being a predictor of a customer's preference for the selected fragrance. In some embodiments, such as those utilizing machine learning or another automated algorithm, the correlation coefficient may be a quantifiable statistical relationship, such as a Pearson correlation coefficient, by comparing data from a large sampling of customers to determine the dependency of one variable, in this case the selected customer characteristic, on a second variable, in this case the selected fragrance. In alternate embodiments such as those using a decision tree or lookup table, a more generalized association between the selected fragrance and the selected customer characteristic may be identified such as a person with a particular customer characteristic being more likely or less likely to purchase a particular fragrance. In some embodiments, associations may be determined based upon manual or digitally collected interviews to ascertain customer preferences and the creation of association definitions based upon subjective or other analyses of the collected data. In an embodiment, an association may comprise gender such as a customer being female and an associated fragrance Her Eau de Parfum. In another embodiment, identifying that a customer characteristic of a fruity fragrance preferences and associating it with the fragrance, My Burberry Eau de Toilette. In some embodiments, multiple customer characteristics may be considered together, such as females with seductive personalities which may be associated with the fragrance, Her Eau de Parfum. Associations represent potential predictive relationships between one or more customer characteristics and one or more fragrances. Saving, at step 714, the associations to the association database 120. Determining, at step 716, whether there are more customer characteristics to be analyzed. In an embodiment, there are additional customer characteristics to be analyzed, such as a customer preference for kayaking. As there are more customer characteristics, returning to step 710 and selecting another customer characteristic. In an alternate embodiment, there are no additional customer characteristics to be analyzed. Determining, at step 718, whether there are more fragrances to be analyzed. In an embodiment, there are additional fragrances, fragrance characteristics, ingredients, etc. to be analyzed, such as the fragrance with ID 173, Brit For Her Eau de Parfum. As there are more fragrances to be analyzed, returning to step 708 and selecting another fragrance. In an alternate embodiment, there are not additional fragrances to be analyzed. Returning, at step 720, to the base module 122.

Figure 8:
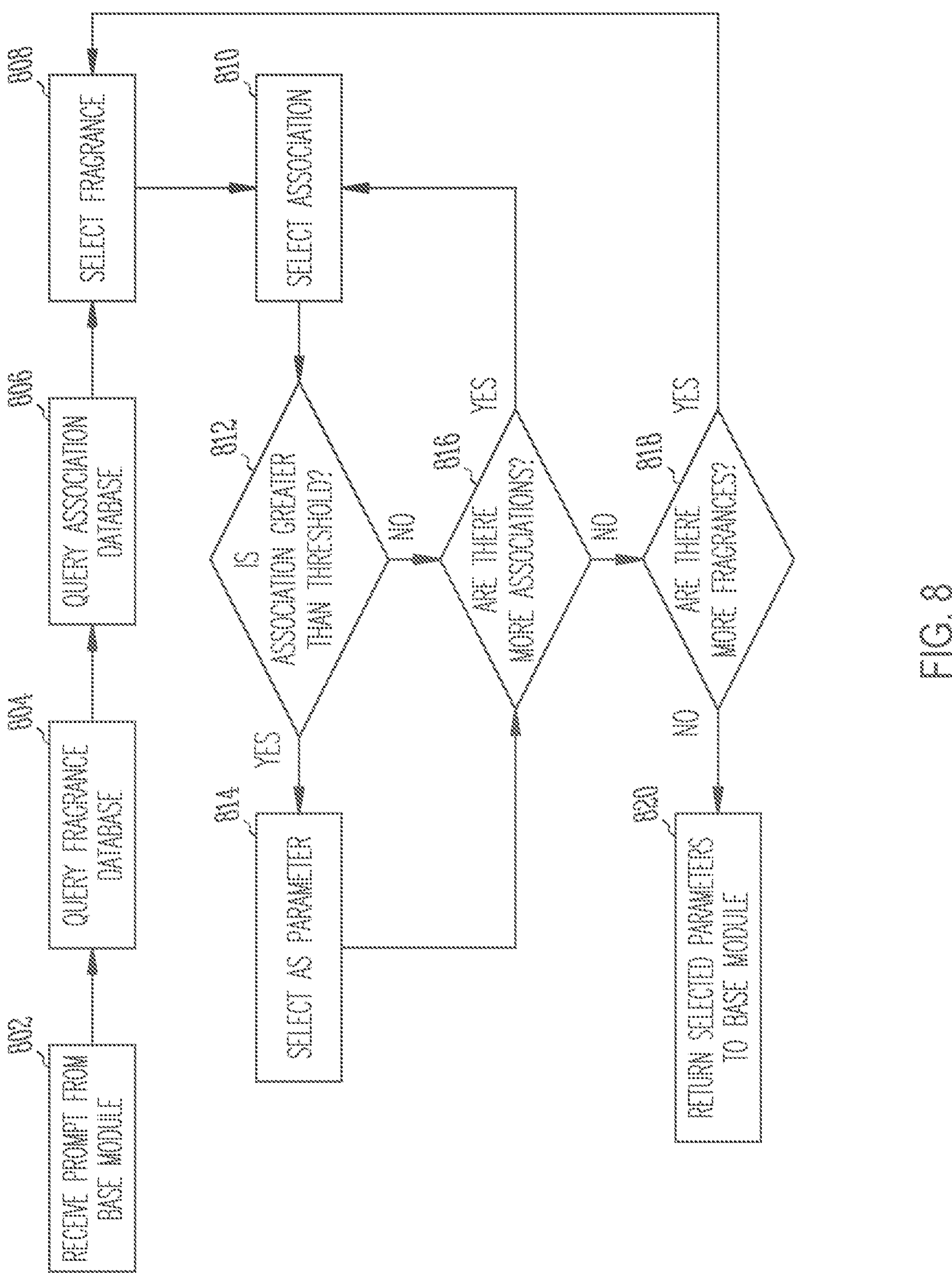

Functioning of the "Parameter Selection Module" will now be explained with reference to FIG. 8. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the parameter selection module 128. The process begins with receiving, at step 802, a prompt from the base module 122. The prompt may include association data from the created by the analysis module 126. The prompt may additionally include instructions pertaining to the type of recommendation engine to be created, for example, whether it is to be used for a group of related fragrances, or alternatively to be used when a type of customer characteristic is identified, such as an interest in outdoor activities. Querying, at step 804, the fragrance database 116 for one or more fragrances, fragrance characteristics, ingredients, etc. Querying, at step 806, the association database 120 for at least one correlation or association between one or more fragrances, fragrance characteristics, ingredients, etc. and one or more customer characteristics. An association may be a correlation coefficient or any other number quantifying the relationship between a fragrance and a customer characteristic or the probability that a customer characteristic is a predictor of a customer's preference for a fragrance. An association may additionally be a non-numerical representation of the relationship between a customer characteristic and a fragrance, fragrance characteristic, ingredients, etc. Selecting, at step 808, a fragrance, fragrance characteristic, or fragrance ingredient from the data retrieved from the fragrance database 116. In an embodiment, selecting the fragrance with ID 11, Her Eau de Parfum. Selecting, at step 810, a correlation or association from the data retrieved from the association database 120. The association comprising at least a customer characteristic and identified relationship with a selected fragrance. The identified relationship may comprise an indication of the strength of the relationship which may be quantitative, such as in the case of a correlation coefficient, ordinal, such as a ranking, or subjective, including descriptors such as low, moderate, or high. Determining, at step 581, whether the association is greater than a threshold. In an embodiment, determining whether a correlation coefficient is above a threshold value. A threshold value may be selected by a system administrator which is then used to determine whether a customer characteristic represented by the correlation coefficient should be selected as a parameter. If the correlation coefficient is above the threshold value, the association may be selected as a parameter, otherwise it will not be selected as a parameter. In some embodiments, a select number of associations will be selected, such as the top 100. In other embodiments, a top percentage, such as the top 10% of associations by correlation coefficient will be selected as parameters. In alternate embodiments, correlation coefficients may not be used, and instead, more generalized associations may be used. For example, an association may be selected, such as customers who like kayaking tend to have a preference for the fragrance with ID 11, Her Eau de Parfum, while the same cohort tends not to have a preference for fragrance with ID 174, Brit For Her Eau de Toilette. These associations may be identified by either direct observations of an individual customer, such as by receiving a survey response indicating that they do not like such fragrances and other such feedback or may be aggregated from customer input and feedback from a large selection of collected data. In the case of aggregated data, the association may be identified if more than half of relevant customers, such as those who were identified as enjoying kayaking, liked fragrance with ID 11. An association would not be identified if fewer than half of customers in the same cohort indicated that they preferred the fragrance. The threshold may be moved and, in some cases, may be subjectively assessed and assigned by a human screener. Other algorithms may be used to determine such associations. When associations are identified, they may be selected as a parameter, otherwise they may be disregarded. In some embodiments, associations may comprise a plurality of customer characteristics and/or fragrances. Selecting, at step 814, the customer characteristic represented by a correlation or association as a parameter if its correlation coefficient is above a threshold value or if there is an association of sufficient significance to be selected by manual selection or other selection algorithms or criteria. For example, selecting 'enjoying kayaking' as a parameter which can be used to identify customers with a preference for the fragrance with ID 11. In some embodiments, a single parameter may be used to make a recommendation. In other embodiments, a plurality of parameters may be used, such as in a decision tree or lookup table. In further embodiments, parameters may be selected to be used to train a machine learning algorithm or to modify the weighting for a weighted values table or process to generate fragrance recommendations. In some embodiments, a parameter may comprise a personality trait, emotion, reaction, etc. which may indicate a preference for the selected fragrance. Selecting the parameter and fragrance may comprise adding the personality trait, emotion, reaction, etc. to a lookup table associated with the selected fragrance, or alternatively may adjust a value weighting to be used in determining whether to recommend the fragrance based upon the parameter. Determining, at step 816, whether there are more associations to be analyzed. In an embodiment, there are additional associations to be analyzed, therefore returning to step 810, and selecting another correlation or association. In an alternate embodiment, there are no additional correlations or associations to be analyzed. Determining, at step 818, whether there are more fragrances to be analyzed. In an embodiment, there are additional fragrances, fragrance characteristics, ingredients, etc. to be analyzed, such as the fragrance with ID 173, Brit For Her Eau de Parfum. As there are more fragrances to be analyzed, returning to step 808 and selecting another fragrance. In an alternate embodiment, there are not additional fragrances to be analyzed. Returning, at step 820, the selected parameters to the base module 122.

Figures 9, 10:
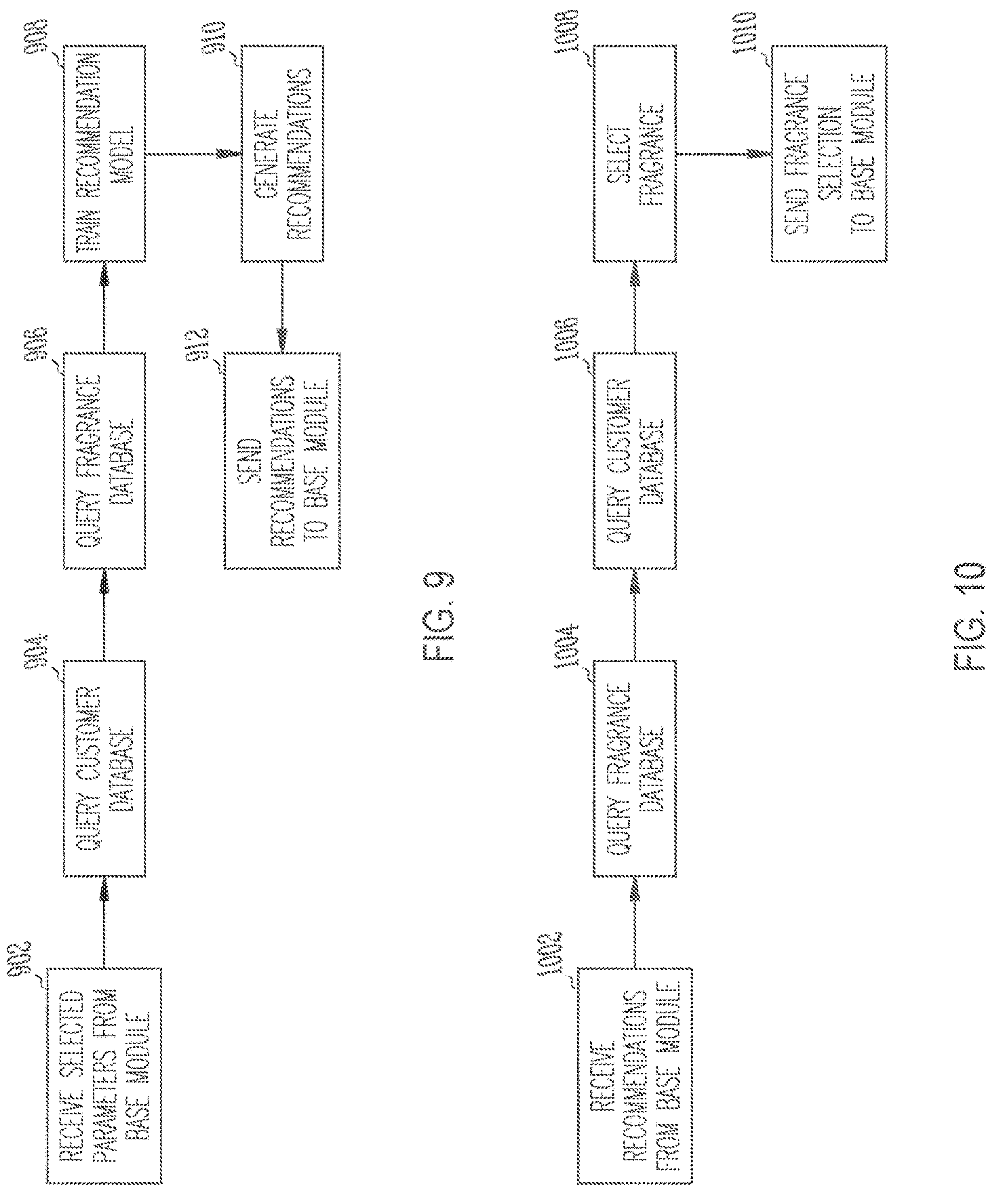

Functioning of the "Recommendation Module" will now be explained with reference to FIG. 9. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the recommendation module 130. The process begins with receiving, at step 902, selected parameters from the base module 122. The selected parameters having met a quantitative threshold or have been selected due to an identified association with at least one fragrance preference. Querying, at step 904, the customer database 118 for customer characteristics corresponding to the selected parameters. For example, a selected parameter may comprise an association between a customer's preference for kayaking and their preference for a fragrance with the ID 11, and the corresponding customer characteristic is the customer preference for kayaking. Additionally retrieving data related to a customer of interest for whom a recommendation is to be generated. The data related to the customer of interest may influence the training of a recommendation model by using only parameters which correspond with the available data describing the customer. For example, if a customer's hobby data is available, then parameters related to hobby preferences would be included in the training data, whereas if social media data is not available for the customer of interest, then social media related parameters would be excluded from the training data. Querying, at step 906, the fragrance database 116 for available fragrances. The fragrance data may include specific fragrances, but may also include their characteristics, ingredients, etc. Any such data describing a fragrance may be utilized in the generation of a recommendation model. For example, fragrances may ultimately be recommended as a family of fragrances, rather than a specific fragrance. Training, at step 908, a recommendation model based upon the customer characteristics corresponding with the selected parameters. In a machine learning application, the customer characteristics would correspond to features, or mapped source data used to train the machine learning model. Training a machine learning model typically uses regression by applying an adjustment or correction after each successive training test. Several evolutions may be completed, with a reserved selection of training data reserved as test data to facilitate assessment of the trained model's accuracy. The evolutions may continue until the model's predictive accuracy is above a threshold value, such as 95%. The reserved training data may be changed, being randomly reselected between each evolution. A recommendation model may alternatively be based upon a lookup table or decision tree. In a lookup table, one or more customer characteristics based upon the selected parameters may be used to map directly to one or more fragrances. In some cases, multiple lookup tables may be available using different combinations of the selected parameters. For example, some tables may use personality traits, while others may use hobbies or interests. Further tables may comprise occasions, while others may comprise a combination of interests and occasions. These tables may be formed by using the selected parameters to map the fragrances to customer characteristics. A decision tree may be created similarly to lookup tables, except instead of looking up matches, a series of branching decisions may be used instead. For example, one decision tree may comprise the user's interests, while another may be the occasion, and a further decision may be the user's stated fragrance preferences. Similar to the lookup tables, the decision tree branching points may be determined based upon a mapping of fragrances to customer characteristics. The selected parameters may be used to modify weightings in a weighted values approach such that a lookup table or algorithm is used where matched customer characteristics may increase or decrease a preference likelihood for one or more fragrances. Generating, at step 910, one or more fragrance recommendations based upon the trained recommendation model and data collected for a customer. The generated recommendations may comprise one or more specific fragrances or may alternatively comprise one or more families of fragrances such that the fragrances in a family possess similar qualities. Likewise, recommendations may be based upon specific ingredients in the fragrances or common characteristics. In some embodiments, recommendations are based upon personality type. In other embodiments, recommendations are based upon declarative preferences of the customer for specific olfactive components or ingredients (e.g., "I prefer floral scents like peony"), including recommendations based on specific fragrances the customer has indicated they currently use or prefer. In further embodiments, recommendations are based upon recommending fragrances with new ingredients that have similar olfactive properties and characteristics. In another embodiment, recommendations are based upon ingredients that are similar to ingredients in the customer's current or preferred fragrance. In other embodiments, recommendations may use a weighting method (singly or in combination) such that preferences and characteristics (such as personality type, mood, an occasion, etc.) are given more or less influence in the rating based upon the olfactive properties or ingredient compositions of fragrances the customer has indicated they prefer or currently use. Fragrance recommendations may comprise a binary recommended vs not recommended decision or may additionally provide a score, for example, each recommended fragrance comprising a likelihood of customer preference out of a score of 10, and recommended fragrances may be any fragrance with a score above a threshold, such as 8/10. These scores may further be used to select one or more fragrances from the recommended fragrances. In an embodiment, determining that a customer being female makes them more likely to prefer Her Eau de Parfum. In another embodiment, identifying that a customer characteristic of a fruity fragrance preferences indicates an increased preference for My Burberry Eau de Toilette. In some embodiments, multiple customer characteristics may be considered together, such as females with seductive personalities have a preference for Her Eau de Parfum. Sending, at step 912, the one or more fragrance recommendations to the base module 122.

Functioning of the "Fragrance Selection Module" will now be explained with reference to FIG. 10. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the fragrance selection module 132. The process begins with receiving, at step 1002, one or more fragrance recommendations from the base module 122. The one or more fragrance recommendations may comprise specific fragrances or groups of fragrances based upon commonalities. Querying, at step 1004, the fragrance database 116 for one or more fragrances corresponding with the fragrance recommendations received from the base module 122. For example, if a group of fragrances was recommended, then identifying each unique fragrance within the group of fragrances as eligible for selection. Querying, at step 1006, the customer database 118, for specific fragrance preferences or information regarding the current recommendation. For example, if the customer desires a new fragrance for an upcoming party and/or would prefer a mild fragrance which would not clash with the scent or flavors of a dinner. Selecting, at step 1008, a fragrance from the fragrance recommendations based upon the customer's preferences. In some embodiments, multiple fragrances may be selected. The fragrance may be selected by automated means using one or more algorithms or may instead be selected manually by a purveyor or the customer. In some embodiments, multiple fragrances may be selected with the intent of blending them into a new fragrance. In alternate embodiments, multiple fragrances may be selected with the intent to send the customer a plurality of fragrances instead of a single fragrance. In some embodiments, a fragrance may be selected using customer data and a weighted values method such as a lookup table or algorithm. In other embodiments, multiple fragrances may be selected based on multiple, differentiated decision pathways as described in FIG. 9. Fragrances may be selected based upon a customer's data being used to make a prediction using a machine learning algorithm to select from the recommended fragrances. Further embodiments may select a fragrance based on similar characteristics to the customer's preferences including a similar olfactive and ingredients. In some embodiments, a fragrance recommendation may include a score indicating the likelihood the fragrance is preferred by a customer. Fragrances may be selected based upon this score, such as the highest scoring fragrance or where multiple fragrances are selected, the top "n" fragrances with the highest recommendation scores. Sending, at step 1010, the selected fragrance, or fragrances to the base module 122.

Figure 11:
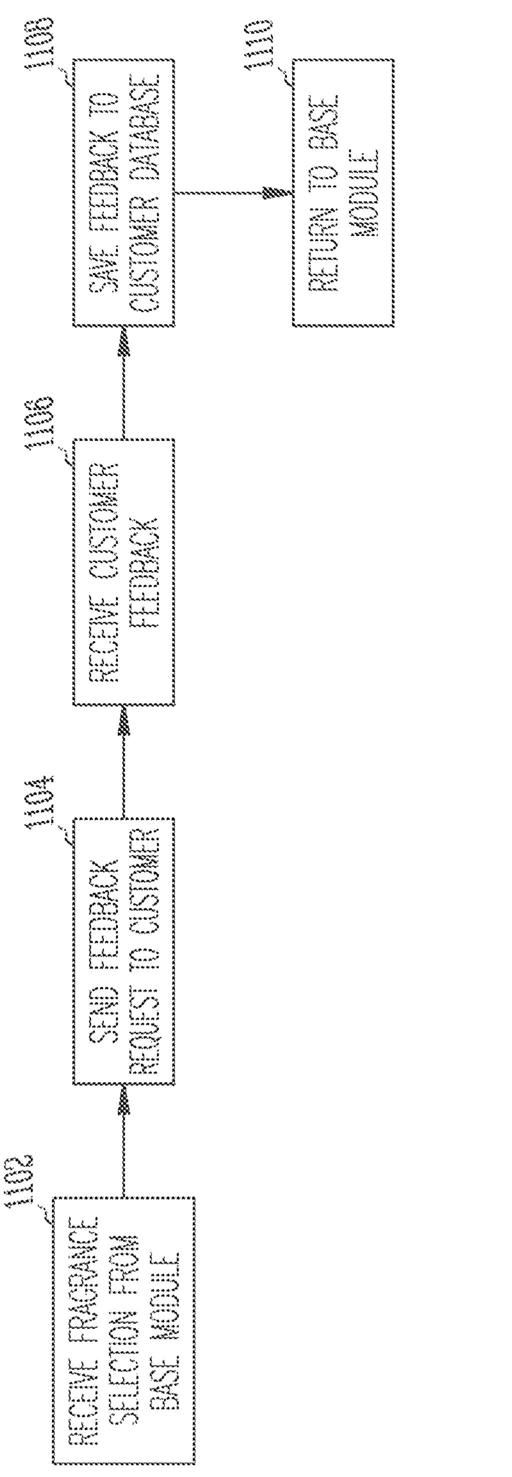

Functioning of the "Feedback Module" will now be explained with reference to FIG. 11. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

This figure displays the feedback module 134. The process begins with receiving, at step 1102, the fragrance selection from the base module. In some embodiments, multiple fragrances may be selected. Receiving the fragrance may comprise providing one or more fragrances to a customer, such as part of a sample to allow the customer to assess the one or more fragrances. In other embodiments, receiving the fragrance may comprise presenting the customer with an opportunity to purchase the one or more fragrances. In another embodiment, the one or more fragrances may be purchased as a gift. In some embodiments, the one or more fragrances may be presented as a notification to the user such as via an email, SMS message, application notification, etc. Said notification or opportunity to purchase may additionally comprise an incentive to buy, such as a discount, rebate, money back guarantee, etc. In a preferred embodiment, the one or more fragrances are selected and provided based upon parameters and/or recommendations customized based upon the customer's available customer characteristics. Sending, at step 1104, a feedback request to the customer. The feedback request may pertain to the selected fragrance or may alternatively be a general inquiry. Examples of a feedback request may be a customer satisfaction survey delivered via mail or email. The feedback request is optional and is not required to practice the invention. The customer may alternatively voluntarily share their feedback via behaviors, such as returning a product or purchasing a product again, or by voluntarily submitting a review, complaint, etc. Receiving, at step 1106, feedback from a customer. Feedback may be explicit, such as from a survey response, review, complaint, etc. or may be obtained passively by observing actions taken by the customer such as whether they purchase a product containing a fragrance, which would indicate a positive response or preference, especially if repeatedly purchasing one or more products with the same fragrance, whereas the customer returning a product with a specific fragrance may indicate a negative response or preference. Customer feedback may also be available via social media posts including mentions, shares, recommendations, and critical reviews. In some embodiments, a plurality of fragrances may be presented to the customer and the customer provides feedback regarding their preferences. The feedback may comprise a ranking of the provided fragrances from most preferred to least preferred. The feedback may alternatively be binary, such as preferred or not preferred, liked or disliked, etc. The feedback may alternatively be an independent scoring, such as 8/10 where 10/10 would represent the highest possible preference and 0/10 would represent the worst or lowest possible preference. Saving, at step 1108, the customer feedback to the customer database 118. Information accumulated in customer database 118 can be used to further refine any of the activities described in FIGS. 6 through 10 for analysis, association, recommendation or selection of fragrances. Returning, at step 1110, to the base module 122.

In a preferred embodiment, a user or customer is provided a plurality of questions to which the customer responds via an input device 110, microphone 108, camera 106, or to which responses are detected via one or more sensors 104. The questions comprising identifying questions in addition to questions indented to help identify the user's personality. Questions may additionally request the customer to declare one or more preferences for one or more fragrances, fragrance characteristics, cosmetic or clothing styles, lifestyles, etc. The customer may additionally be requested to select one or more fragrances which they are currently using or would like to use. The customer may additionally rank their fragrance preferences and/or the fragrances they are currently using in an ordinal fashion. One or more images may be acquired, either via one or more cameras 106, or via a file upload. The one or more images are analyzed to determine one or more personality characteristics, or an alternate approach to images may be used, such as video footage or questionnaire, to determine one or more personality characteristics. One or more recommendation pathways are identified from the information provided by the customer. Examples include personality, scent similarity to currently used fragrances, similarity to declared preferences, ingredient similarity to currently used fragrances, a combination of personality and scent similarity to currently used fragrances using weighted values, and personality and ingredient similarity to currently used fragrances. A fragrance recommendation may be selected for at least one of each of the recommendation pathways. For example, a user's personality may be identified as adventurous, and a matching fragrance recommendation may be Her Eau de Parfum. The selected recommendations may be provided to the customer, from whom feedback may be received and used to assess the relevancy of the selected recommendations.

Figure 12:
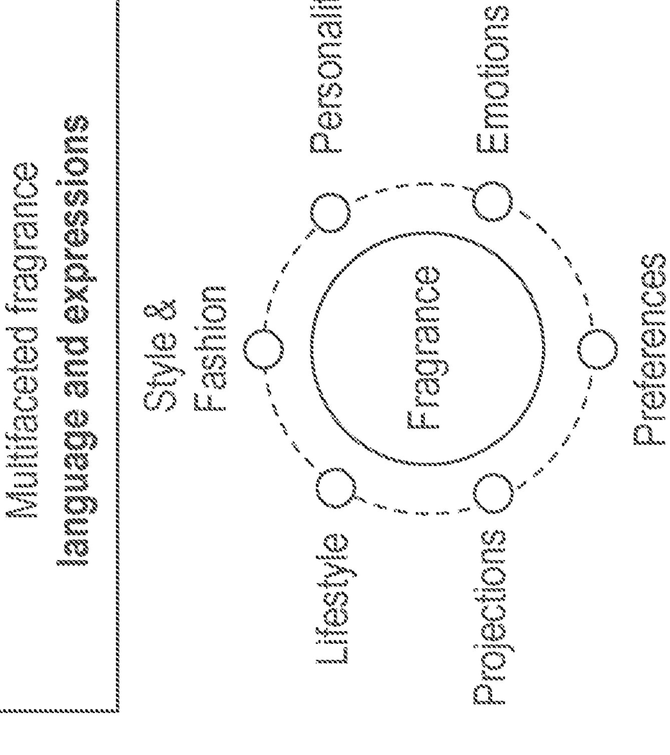

FIG. 12 illustrates fragrance as a beauty and style proposition, according to an embodiment. FIG. 12 shows fragrance as part of an overall beauty and style proposition for various occasions and multifaceted fragrance language and expressions.

FIG. 13 illustrates components of fragrance recommendation, according to an embodiment. FIG. 13 shows experience, service, content, and product components of a fragrance recommendation system.

Figure 14:
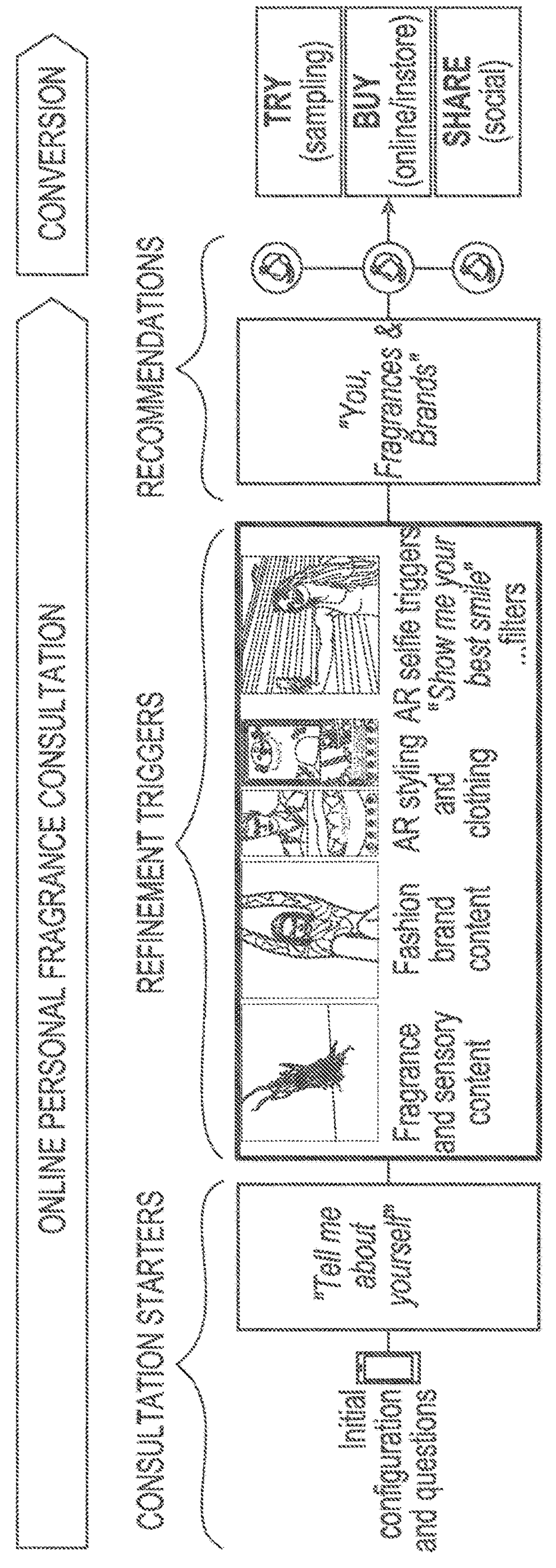

FIG. 14 illustrates an example of a workflow for making a fragrance recommendation, according to an embodiment. FIG. 14 shows an online personal fragrance consultation workflow for a fragrance recommendation system.

Figure 15:
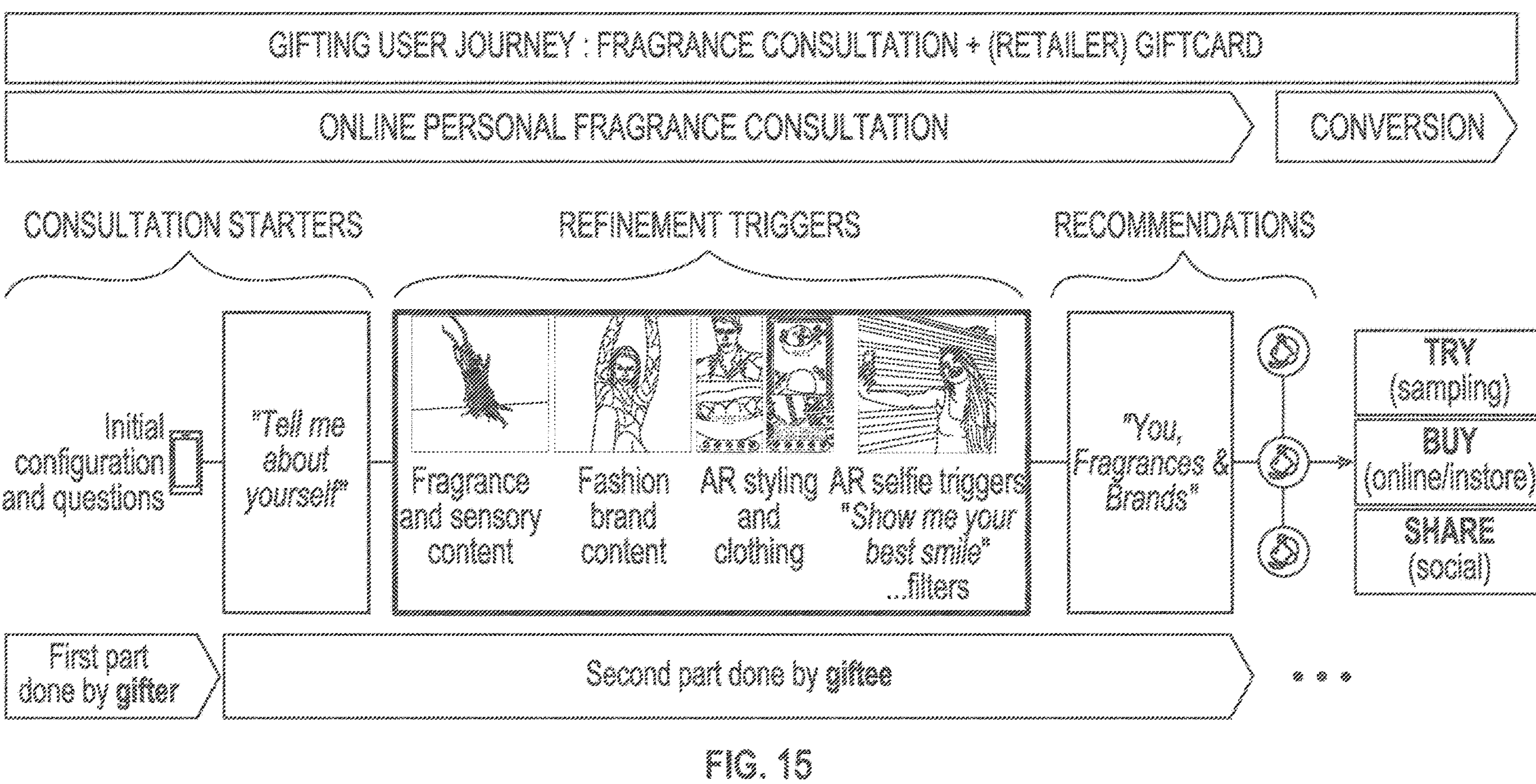

FIG. 15 illustrates an example of a gifting workflow for making a fragrance recommendation, according to an embodiment. FIG. 15 shows a gifting workflow for a fragrance recommendation system.

Figure 16:
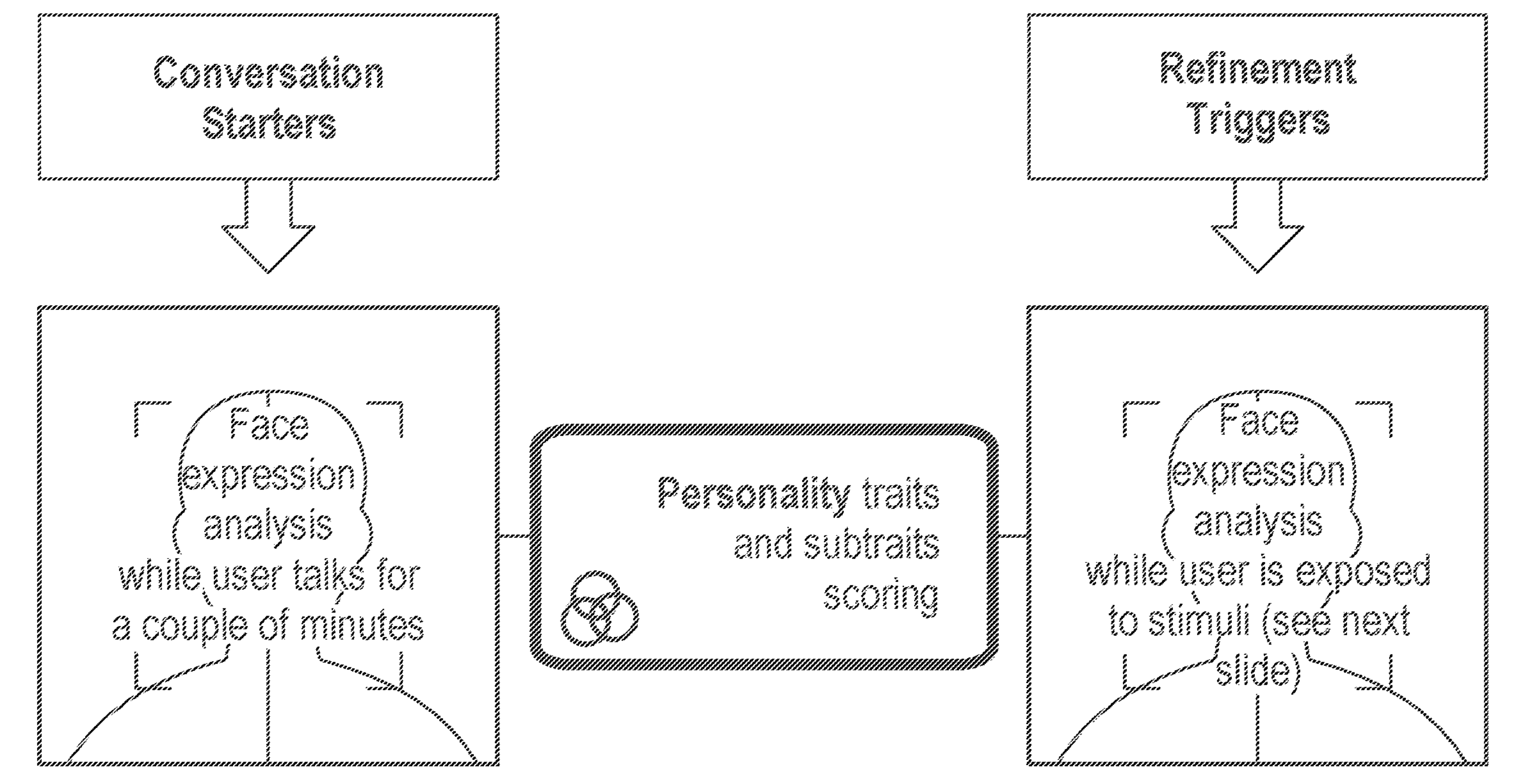

FIG. 16 illustrates an example of a personality link between conversation starters and refinement triggers, according to an embodiment. FIG. 16 shows a personality traits and sub traits scoring link between conversation starters and refinement triggers.

Figure 17:
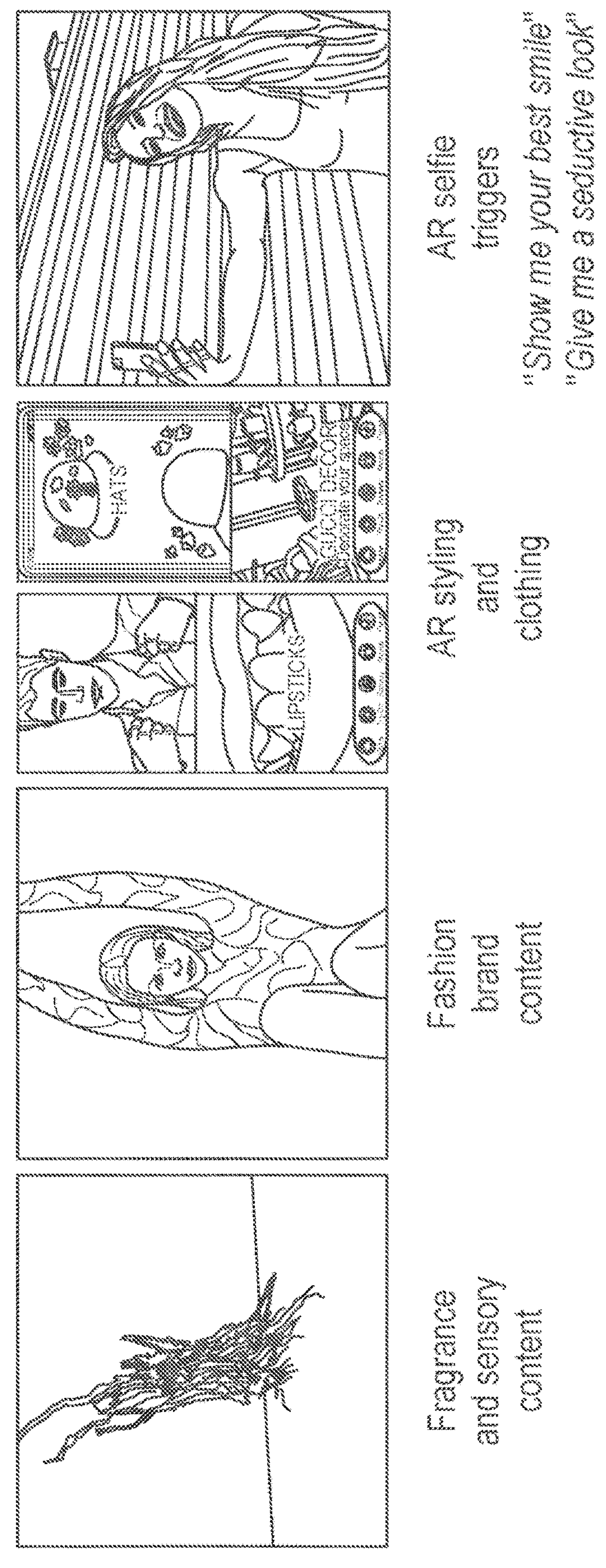

FIG. 17 illustrates examples of refinement triggers, according to an embodiment. FIG. 17 shows examples of stimuli or activities to which a user is exposed while performing facial analysis to observe and determine user reaction to the stimuli or activities.

FIG. 18 illustrates an example of customer to product mapping, according to an embodiment. FIG. 18 shows mapping of consumers to products using consumer profiles, brand archetypes, fragrance usage and attitude, education scent personalities, and data science iterations.

FIG. 19 illustrates an example of a scent to personality database, according to an embodiment. FIG. 19 shows an example database architecture for mapping scents to personality keywords.

FIGS. 20A, 21B, and 21C illustrate classification of personality traits, according to an embodiment. FIGS. 20A to 20C show examples of keyword groupings for attitude, feeling, and perception personality dimensions.

FIG. 21 illustrates an example of keyword grouping, according to an embodiment. FIG. 21 shows examples personality traits mapped to keyword groupings.

Figure 22:
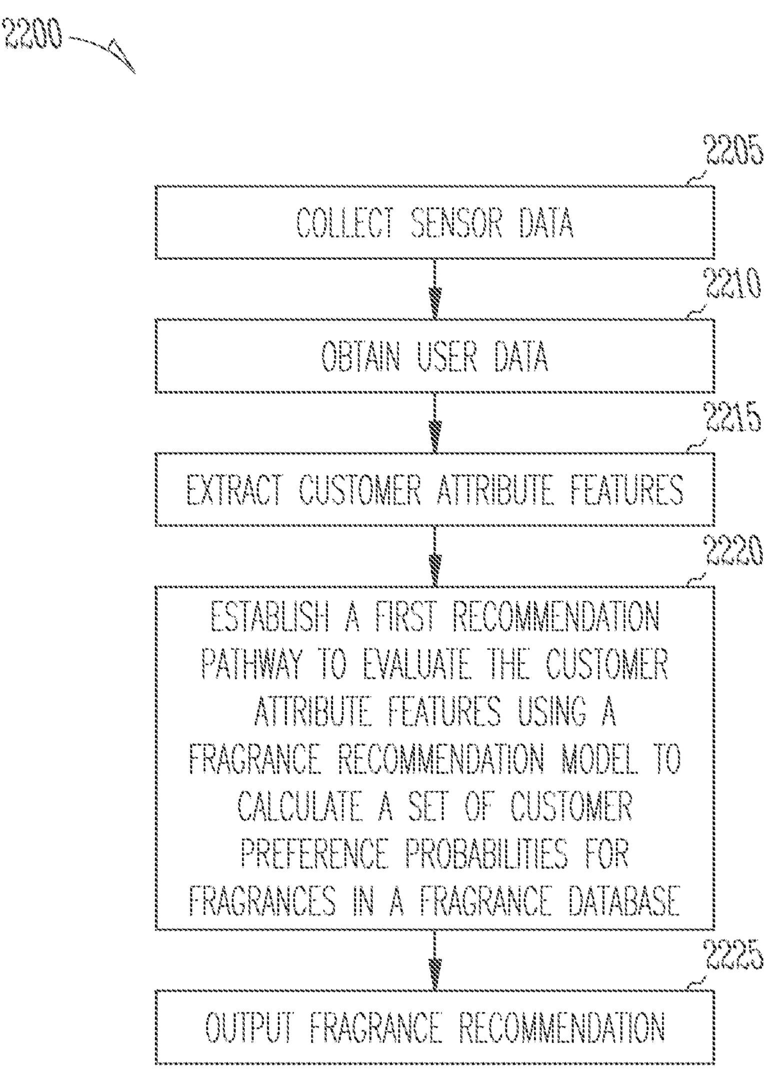
FIG. 22 is a flow diagram of an example of a method for making a fragrance recommendation, according to an embodiment.

FIG. 22 is a flow diagram of an example of a method 2200 for making a fragrance recommendation, according to an embodiment. The method 2200 may provide features as described in FIGS. 1 to 22.

At operation 2205, sensor data is collected from a sensor array of a user computing device. In an example, the user computing device may be a mobile computing device, a smartphone, a tablet computing device, a laptop computing device, a desktop computing device, or a kiosk.

At operation 2210, user data is obtained for a user associated with the user computing device. In an example, the user data may include a gender of the user, hobbies of the user, personality traits of the user, fragrance preferences of the user, purchase history of the user, or product feedback submitted by the user.

At operation 2215, customer attribute features are extracted from the sensor data and the user data. In an example, the customer attribute features may include at least one human parameter and at least one non-human parameter. In an example, the sensor data is evaluated to determine a current emotional state of the user and the current emotional state is added to the customer attribute features. In an example, an image of the user may be obtained from the sensor data and facial features may be detected in the image. The facial features may be evaluated to determine a customer attribute feature and the customer attribute feature may be added to the customer attribute features. In an example, a genetic profile may be obtained for the user. The genetic profile may be evaluated to identify genetic customer attribute features and the genetic customer attribute features may be added to the customer attribute features. In an example, social media data may be extracted from the user data. Social media profiles may be identified using the social media data. Characteristic data may be obtained using the social media profiles. Social media attribute features may be extracted from the characteristic data and the social media attribute features may be added to the customer attribute features. In an example, environmental condition data may be obtained for an environment of the user. Environmental attribute features may be extracted from the environmental condition data and the environmental attribute features may be added to the customer attribute features. In an example, a video feed may be obtained from the sensor array. The video feed may be processed using an artificial intelligence processor to identify an emotional reaction of the user to a stimuli present in the video feed. An emotive reaction attribute feature may be generated for the user based on the identified emotional reaction and the emotive reaction feature may be added to the customer attribute features. In an example, an air sample may be collected using a volatile organic compound (VOC) sensor. The air sample may be evaluated to identify concentrations of a set of VOCs. The fragrance database may be queried using the concentrations of the set of VOCs to identify a present fragrance. Fragrance attribute features may be obtained for the present fragrance from the fragrance database and the fragrance attribute features may be added to the customer attribute features. In an example, social proximity data may be obtained for the user. The social proximity data may be evaluated to identify a connection between the user and a connection. Connection data may be collected for the connection. Connection attribute features may be extracted from the connection data and the connection attribute features may be added to the customer attribute features. In an example, an event may be identified in the user data. The user data may be evaluated to collect event data. Event attribute features may be extracted from the event data and the event attribute features may be added to the customer attribute features.

At operation 2220, a first recommendation pathway is established to evaluate the customer attribute features using a fragrance recommendation model to calculate a set of customer preference probabilities for fragrances in a fragrance database. In an example, fragrance user characteristic training data is obtained and the fragrance recommendation model is trained to calculate customer preference probabilities for fragranced based on customer characteristics using the fragrance user characteristic training data. In an example, reaction data may be captured from the sensor array in response to presentation of a stimuli to the user via the display. Reaction attribute features may be extracted from the reaction data and the reaction attribute features may be evaluated in conjunction with the customer attribute features to calculate the set of customer preference probabilities. In an example, the customer attribute features may be evaluated to assign the user to a preference group and the fragrance recommendation may be selected using the set of customer preference probabilities and the preference group. In an example, a first correlation coefficient may be calculated for a first feature of the customer attribute features and a second correlation coefficient may be calculated for a second feature of the customer attribute features. It may be determined that the first correlation coefficient is outside a correlation coefficient threshold and the second correlation coefficient is within the correlation coefficient. The second feature may be ignored and the first feature may be evaluated using the fragrance recommendation model.

At operation 2225, a fragrance recommendation is output to the user, via a display of the user computing device, based on the set of customer preference probabilities. In an example, the set of customer preference probabilities may be compared to a sample fragrance library to select a set of fragrance samples for the user. A notification message may be generated for the user with a recommendation notification that includes identification of the set of fragrance samples and the notification message may be transmitted to a device of the user.

In an example, a response request prompt may be transmitted transmitting to an output device of the user computing device in conjunction with the fragrance recommendation. A response to the response request may be received via an input device of the user computing device. A second recommendation pathway may be established to evaluate the fragrance database using preference parameters determined from the response. The fragrance database may be evaluated using the preference parameters to select an alternate fragrance recommendation and the alternate fragrance recommendation may be output to the user via a display of the user computing device.

In an example, a genetic profile may be obtained for the user and an ingredient list may be obtained for the fragrance. The genetic profile may be evaluated to generate a prediction of an allergic rection to an ingredient in the ingredient list. Recommendation of the fragrance may be prevented based on the prediction of the allergic reaction and an alternate fragrance may be selected based on the genetic profile and the set of customer preference probabilities.

In an example, a feedback request prompt may be transmitted to an output device of the user computing device in conjunction with the fragrance recommendation. Feedback regarding the fragrance recommendation may be received from the user via an input device of the user computing device and the fragrance recommendation model may be refined using the feedback.

In an example, a personality fragrance prediction model may be trained using a corpus of training data including personality traits and corresponding fragrance preferences. A fragrance attribute of a fragrance from the fragrance database may be evaluated using the personality fragrance prediction model to predict one or more personality traits associated with the fragrance attribute and the predicted one or more personality traits associated with the fragrance attribute may be stored in the fragrance database.

Figure 23:
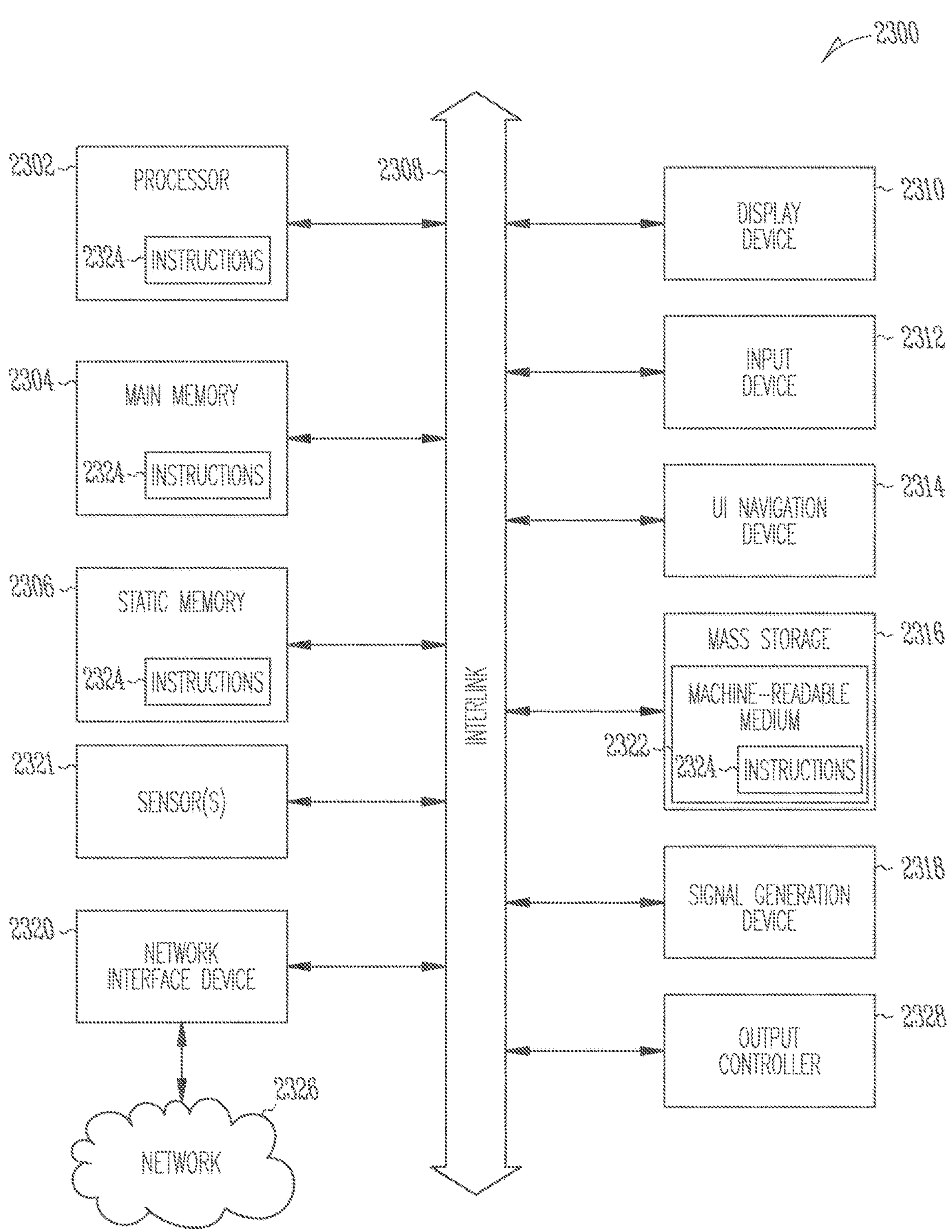
FIG. 23 is a block diagram illustrating an example of a machine upon which one or more embodiments may be implemented.

FIG. 23 illustrates a block diagram of an example machine 2300 upon which any one or more of the techniques (e.g., methodologies) discussed herein may perform. In alternative embodiments, the machine 2300 may operate as a standalone device or may be connected (e.g., networked) to other machines. In a networked deployment, the machine 2300 may operate in the capacity of a server machine, a client machine, or both in server-client network environments. In an example, the machine 2300 may act as a peer machine in peer-to-peer (P2P) (or other distributed) network environment. The machine 2300 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term “machine” shall also be taken to include any collection of machines that individually or jointly execute a set (or multiple sets) of instructions to perform any one or more of the methodologies discussed herein, such as cloud computing, software as a service (Saas), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 2300 may include a hardware processor 2302 (e.g., a central processing unit (CPU), a graphics processing unit (GPU), a hardware processor core, or any combination thereof), a main memory 2304 and a static memory 2306, some or all of which may communicate with each other via an interlink (e.g., bus) 2308. The machine 2300 may further include a display unit 2310, an alphanumeric input device 2312 (e.g., a keyboard), and a user interface (UI) navigation device 2314 (e.g., a mouse). In an example, the display unit 2310, input device 2312 and UI navigation device 2314 may be a touch screen display. The machine 2300 may additionally include a storage device (e.g., drive unit) 2316, a signal generation device 2318 (e.g., a speaker), a network interface device 2320, and one or more sensors 2321, such as a global positioning system (GPS) sensor, compass, accelerometer, or other sensors. The machine 2300 may include an output controller 2328, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 2316 may include a machine readable medium 2322 on which is stored one or more sets of data structures or instructions 2324 (e.g., software) embodying or utilized by any one or more of the techniques or functions described herein. The instructions 2324 may also reside, completely or at least partially, within the main memory 2304, within static memory 2306, or within the hardware processor 2302 during execution thereof by the machine 2300. In an example, one or any combination of the hardware processor 2302, the main memory 2304, the static memory 2306, or the storage device 2316 may constitute machine readable media.

While the machine readable medium 2322 is illustrated as a single medium, the term "machine readable medium" may include a single medium or multiple media (e.g., a centralized or distributed database, and/or associated caches and servers) configured to store the one or more instructions 2324.

The term "machine readable medium" may include any medium that is capable of storing, encoding, or carrying instructions for execution by the machine 2300 and that cause the machine 2300 to perform any one or more of the techniques of the present disclosure, or that is capable of storing, encoding or carrying data structures used by or associated with such instructions. Non-limiting machine readable medium examples may include solid-state memories, and optical and magnetic media. In an example, machine readable media may exclude transitory propagating signals (e.g., non-transitory machine-readable storage media). Specific examples of non-transitory machine-readable storage media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 2324 may further be transmitted or received over a communications network 2326 using a transmission medium via the network interface device 2320 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, LoRa®/LoRaWAN® LPWAN standards, etc.), IEEE 802.15.4 family of standards, peer-to-peer (P2P) networks, 3rd Generation Partnership Project (3GPP) standards for 4G and 5G wireless communication including: 3GPP Long-Term evolution (LTE) family of standards, 3GPP LTE Advanced family of standards, 3GPP LTE Advanced Pro family of standards, 3GPP New Radio (NR) family of standards, among others. In an example, the network interface device 2320 may include one or more physical jacks (e.g., Ethernet, coaxial, or phone jacks) or one or more antennas to connect to the communications network 2326. In an example, the network interface device 2320 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 2300, and includes digital or analog communications signals or other intangible medium to facilitate communication of such software.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

ADDITIONAL EXAMPLES

Example 1 is a method executable by computing circuitry comprising: collecting sensor data from a sensor array of a user computing device; obtaining user data for a user associated with the user computing device; extracting customer attribute features from the sensor data and the user data; establishing a first recommendation pathway to evaluate the customer attribute features using a fragrance recommendation model to calculate a set of customer preference probabilities for fragrances in a fragrance database; and outputting a fragrance recommendation to the user, via a display of the user computing device, based on the set of customer preference probabilities.

In Example 2, the subject matter of Example 1 includes, obtaining fragrance user characteristic training data; and training the fragrance recommendation model to calculate customer preference probabilities for fragranced based on customer characteristics using the fragrance user characteristic training data.

In Example 3, the subject matter of Examples 1-2 includes, evaluating the sensor data to determine a current emotional state of the user; and adding the current emotional state to the customer attribute features.

In Example 4, the subject matter of Examples 1-3 wherein, the user computing device is a mobile computing device, a smartphone, a tablet computing device, a laptop computing device, a desktop computing device, or a kiosk.

In Example 5, the subject matter of Examples 1-4 includes, in response to presentation of a stimuli to the user via the display, capturing reaction data from the sensor array; extracting reaction attribute features from the reaction data; and evaluating the reaction attribute features in conjunction with the customer attribute features to calculate the set of customer preference probabilities.

In Example 6, the subject matter of Examples 1-5 wherein, the user data includes a gender of the user, hobbies of the user, personality traits of the user, fragrance preferences of the user, purchase history of the user, or product feedback submitted by the user.

In Example 7, the subject matter of Examples 1-6 includes, obtaining an image of the user from the sensor data; detecting facial features in the image; evaluating the facial features to determine a customer attribute feature; and adding the customer attribute feature to the customer attribute features.

In Example 8, the subject matter of Examples 1-7 includes, comparing the set of customer preference probabilities to a sample fragrance library to select a set of fragrance samples for the user; generating a notification message for the user with a recommendation notification that includes identification of the set of fragrance samples; and transmitting a notification message to a device of the user.

In Example 9, the subject matter of Examples 1-8 includes, obtaining a genetic profile for the user; obtaining an ingredient list for the fragrance; evaluating the genetic profile to generate a prediction of an allergic rection to an ingredient in the ingredient list; preventing recommendation of the fragrance based on the prediction of the allergic reaction; and selecting an alternate fragrance based on the genetic profile and the set of customer preference probabilities.

In Example 10, the subject matter of Examples 1-9 includes, obtaining a genetic profile for the user; evaluating the genetic profile to identify genetic customer attribute features; and adding the genetic customer attribute features to the customer attribute features.

In Example 11, the subject matter of Examples 1-10 includes, extracting social media data from the user data; identifying social media profiles using the social media data; obtaining characteristic data using the social media profiles; extracting social media attribute features from the characteristic data; and adding the social media attribute features to the customer attribute features.

In Example 12, the subject matter of Examples 1-11 includes, obtaining environmental condition data for an environment of the user; extracting environmental attribute features from the environmental condition data; and adding the environmental attribute features to the customer attribute features.

In Example 13, the subject matter of Examples 1-12 includes, evaluating the customer attribute features to assign the user to a preference group; and selecting the fragrance recommendation using the set of customer preference probabilities and the preference group.

In Example 14, the subject matter of Examples 1-13 includes, obtaining a video feed from the sensor array; processing the video feed using an artificial intelligence processor to identify an emotional reaction of the user to a stimuli present in the video feed; generating an emotive reaction attribute feature for the user based on the identified emotional reaction; and adding the emotive reaction feature to the customer attribute features.

In Example 15, the subject matter of Examples 1-14 includes, collecting an air sample using a volatile organic compound (VOC) sensor; evaluating the air sample to identify concentrations of a set of VOCs; querying the fragrance database using the concentrations of the set of VOCs to identify a present fragrance; obtaining fragrance attribute features for the present fragrance from the fragrance database; and adding the fragrance attribute features to the customer attribute features.

In Example 16, the subject matter of Examples 1-15 includes, obtaining social proximity data for the user; evaluating the social proximity data to identify a connection between the user and a connection; collecting connection data for the connection; extracting connection attribute features from the connection data; and adding the connection attribute features to the customer attribute features.

In Example 17, the subject matter of Examples 1-16 includes, calculating a first correlation coefficient for a first feature of the customer attribute features and a second correlation coefficient for a second feature of the customer attribute features; determining that the first correlation coefficient is outside a correlation coefficient threshold and the second correlation coefficient is within the correlation coefficient; ignoring the second feature; and evaluating the first feature using the fragrance recommendation model.

In Example 18, the subject matter of Examples 1-17 includes, transmitting, to an output device of the user computing device, a response request prompt in conjunction with the fragrance recommendation; receiving, via an input device of the user computing device, a response to the response request; establishing a second recommendation pathway to evaluate the fragrance database using preference parameters determined from the response; evaluating the fragrance database using the preference parameters to select an alternate fragrance recommendation; and outputting the alternate fragrance recommendation to the user via a display of the user computing device.

In Example 19, the subject matter of Examples 1-18 wherein, the customer attribute features include at least one human parameter and at least one non-human parameter.

In Example 20, the subject matter of Examples 1-19 includes, transmitting, to an output device of the user computing device, a feedback request prompt in conjunction with the fragrance recommendation; receiving, via an input device of the user computing device, feedback regarding the fragrance recommendation from the user; and refining the fragrance recommendation model using the feedback.

In Example 21, the subject matter of Examples 1-20 includes, identifying an event in the user data; evaluating the user data to collect event data; extracting event attribute features from the event data; and adding the event attribute features to the customer attribute features.

In Example 22, the subject matter of Examples 1-21 includes, training a personality fragrance prediction model using a corpus of training data including personality traits and corresponding fragrance preferences; evaluating a fragrance attribute of a fragrance from the fragrance database using the personality fragrance prediction model to predict one or more personality traits associated with the fragrance attribute; and storing the predicted one or more personality traits associated with the fragrance attribute in the fragrance database.

Example 23 is a system comprising means to perform any method of Examples 1-22.

Example 24 is at least one machine-readable medium including instructions that, when executed by a machine, cause the machine to perform any method of Examples 1-22.

Example 25 is a system comprising: at least one processor; and memory comprising instructions that, when executed by the at least one processor, cause the at least one processor to perform operations to: collect sensor data from a sensor array of a user computing device; obtain user data for a user associated with the user computing device; extract customer attribute features from the sensor data and the user data; establish a first recommendation pathway to evaluate the customer attribute features using a fragrance recommendation model to calculate a set of customer preference probabilities for fragrances in a fragrance database; and output a fragrance recommendation to the user, via a display of the user computing device, based on the set of customer preference probabilities.

In Example 26, the subject matter of Example 25 includes, the memory further comprising instructions that, when executed by the at least one processor, cause the at least one processor to perform operations to: obtain fragrance user characteristic training data; and train the fragrance recommendation model to calculate customer preference probabilities for fragranced based on customer characteristics using the fragrance user characteristic training data.

In Example 27, the subject matter of Examples 25-26 includes, the memory further comprising instructions that, when executed by the at least one processor, cause the at least one processor to perform operations to: evaluate the sensor data to determine a current emotional state of the user; and add the current emotional state to the customer attribute features.

In Example 28, the subject matter of Examples 25-27 wherein, the user computing device is a mobile computing device, a smartphone, a tablet computing device, a laptop computing device, a desktop computing device, or a kiosk.

In Example 29, the subject matter of Examples 25-28 includes, the memory further comprising instructions that, when executed by the at least one processor, cause the at least one processor to perform operations to: in response to presentation of a stimuli to the user via the display, capture reaction data from the sensor array; extract reaction attribute features from the reaction data; and evaluate the reaction attribute features in conjunction with the customer attribute features to calculate the set of customer preference probabilities.

In Example 30, the subject matter of Examples 25-29 wherein, the user data includes a gender of the user, hobbies of the user, personality traits of the user, fragrance preferences of the user, purchase history of the user, or product feedback submitted by the user.

In Example 31, the subject matter of Examples 25-30 includes, the memory further comprising instructions that, when executed by the at least one processor, cause the at least one processor to perform operations to: obtain an image of the user from the sensor data; detect facial features in the image; evaluate the facial features to determine a customer attribute feature; and add the customer attribute feature to the customer attribute features.

In Example 32, the subject matter of Examples 25-31 includes, the memory further comprising instructions that, when executed by the at least one processor, cause the at least one processor to perform operations to: compare the set of customer preference probabilities to a sample fragrance library to select a set of fragrance samples for the user; generate a notification message for the user with a recommendation notification that includes identification of the set of fragrance samples; and transmit a notification message to a device of the user.

In Example 33, the subject matter of Examples 25-32 includes, the memory further comprising instructions that, when executed by the at least one processor, cause the at least one processor to perform operations to: obtain a genetic profile for the user; obtain an ingredient list for the fragrance; evaluate the genetic profile to generate a prediction of an allergic rection to an ingredient in the ingredient list; prevent recommendation of the fragrance based on the prediction of the allergic reaction; and select an alternate fragrance based on the genetic profile and the set of customer preference probabilities.

In Example 34, the subject matter of Examples 25-33 includes, the memory further comprising instructions that, when executed by the at least one processor, cause the at least one processor to perform operations to: obtain a genetic profile for the user; evaluate the genetic profile to identify genetic customer attribute features; and add the genetic customer attribute features to the customer attribute features.

In Example 35, the subject matter of Examples 25-34 includes, the memory further comprising instructions that, when executed by the at least one processor, cause the at least one processor to perform operations to: extract social media data from the user data; identify social media profiles using the social media data; obtain characteristic data using the social media profiles; extract social media attribute features from the characteristic data; and add the social media attribute features to the customer attribute features.

In Example 36, the subject matter of Examples 25-35 includes, the memory further comprising instructions that, when executed by the at least one processor, cause the at least one processor to perform operations to: obtain environmental condition data for an environment of the user; extract environmental attribute features from the environmental condition data; and add the environmental attribute features to the customer attribute features.

In Example 37, the subject matter of Examples 25-36 includes, the memory further comprising instructions that, when executed by the at least one processor, cause the at least one processor to perform operations to: evaluate the customer attribute features to assign the user to a preference group; and select the fragrance recommendation using the set of customer preference probabilities and the preference group.

In Example 38, the subject matter of Examples 25-37 includes, the memory further comprising instructions that, when executed by the at least one processor, cause the at least one processor to perform operations to: obtain a video feed from the sensor array; process the video feed using an artificial intelligence processor to identify an emotional reaction of the user to a stimuli present in the video feed; generate an emotive reaction attribute feature for the user based on the identified emotional reaction; and add the emotive reaction feature to the customer attribute features.

In Example 39, the subject matter of Examples 25-38 includes, the memory further comprising instructions that, when executed by the at least one processor, cause the at least one processor to perform operations to: collect an air sample using a volatile organic compound (VOC) sensor; evaluate the air sample to identify concentrations of a set of VOCs; query the fragrance database using the concentrations of the set of VOCs to identify a present fragrance; obtain fragrance attribute features for the present fragrance from the fragrance database; and add the fragrance attribute features to the customer attribute features.

In Example 40, the subject matter of Examples 25-39 includes, the memory further comprising instructions that, when executed by the at least one processor, cause the at least one processor to perform operations to: obtain social proximity data for the user; evaluate the social proximity data to identify a connection between the user and a connection; collect connection data for the connection; extract connection attribute features from the connection data; and add the connection attribute features to the customer attribute features.

In Example 41, the subject matter of Examples 25-40 includes, the memory further comprising instructions that, when executed by the at least one processor, cause the at least one processor to perform operations to: calculate a first correlation coefficient for a first feature of the customer attribute features and a second correlation coefficient for a second feature of the customer attribute features; determine that the first correlation coefficient is outside a correlation coefficient threshold and the second correlation coefficient is within the correlation coefficient; ignore the second feature; and evaluate the first feature using the fragrance recommendation model.

In Example 42, the subject matter of Examples 25-41 includes, the memory further comprising instructions that, when executed by the at least one processor, cause the at least one processor to perform operations to: transmit, to an output device of the user computing device, a response request prompt in conjunction with the fragrance recommendation; receive, via an input device of the user computing device, a response to the response request; establish a second recommendation pathway to evaluate the fragrance database using preference parameters determined from the response; evaluate the fragrance database using the preference parameters to select an alternate fragrance recommendation; and output the alternate fragrance recommendation to the user via a display of the user computing device.

In Example 43, the subject matter of Examples 25-42 wherein, the customer attribute features include at least one human parameter and at least one non-human parameter.

In Example 44, the subject matter of Examples 25-43 includes, the memory further comprising instructions that, when executed by the at least one processor, cause the at least one processor to perform operations to: transmit, to an output device of the user computing device, a feedback request prompt in conjunction with the fragrance recommendation; receive, via an input device of the user computing device, feedback regarding the fragrance recommendation from the user; and refine the fragrance recommendation model using the feedback.

In Example 45, the subject matter of Examples 25-44 includes, the memory further comprising instructions that, when executed by the at least one processor, cause the at least one processor to perform operations to: identify an event in the user data; evaluate the user data to collect event data; extract event attribute features from the event data; and add the event attribute features to the customer attribute features.

In Example 46, the subject matter of Examples 25-45 includes, the memory further comprising instructions that, when executed by the at least one processor, cause the at least one processor to perform operations to: train a personality fragrance prediction model using a corpus of training data including personality traits and corresponding fragrance preferences; evaluate a fragrance attribute of a fragrance from the fragrance database using the personality fragrance prediction model to predict one or more personality traits associated with the fragrance attribute; and store the predicted one or more personality traits associated with the fragrance attribute in the fragrance database.

Example 47 is at least one non-transitory machine-readable medium comprising instructions that, when executed by at least one processor, cause the at least one processor to perform operations to: collect sensor data from a sensor array of a user computing device; obtain user data for a user associated with the user computing device; extract customer attribute features from the sensor data and the user data; establish a first recommendation pathway to evaluate the customer attribute features using a fragrance recommendation model to calculate a set of customer preference probabilities for fragrances in a fragrance database; and output a fragrance recommendation to the user, via a display of the user computing device, based on the set of customer preference probabilities.

In Example 48, the subject matter of Example 47 includes, instructions that, when executed by the at least one processor, cause the at least one processor to perform operations to: obtain fragrance user characteristic training data; and train the fragrance recommendation model to calculate customer preference probabilities for fragranced based on customer characteristics using the fragrance user characteristic training data.

In Example 49, the subject matter of Examples 47-48 includes, instructions that, when executed by the at least one processor, cause the at least one processor to perform operations to: evaluate the sensor data to determine a current emotional state of the user; and add the current emotional state to the customer attribute features.

In Example 50, the subject matter of Examples 47-49 wherein, the user computing device is a mobile computing device, a smartphone, a tablet computing device, a laptop computing device, a desktop computing device, or a kiosk.

In Example 51, the subject matter of Examples 47-50 includes, instructions that, when executed by the at least one processor, cause the at least one processor to perform operations to: in response to presentation of a stimuli to the user via the display, capture reaction data from the sensor array; extract reaction attribute features from the reaction data; and evaluate the reaction attribute features in conjunction with the customer attribute features to calculate the set of customer preference probabilities.

In Example 52, the subject matter of Examples 47-51 wherein, the user data includes a gender of the user, hobbies of the user, personality traits of the user, fragrance preferences of the user, purchase history of the user, or product feedback submitted by the user.

In Example 53, the subject matter of Examples 47-52 includes, instructions that, when executed by the at least one processor, cause the at least one processor to perform operations to: obtain an image of the user from the sensor data; detect facial features in the image; evaluate the facial features to determine a customer attribute feature; and add the customer attribute feature to the customer attribute features.

In Example 54, the subject matter of Examples 47-53 includes, instructions that, when executed by the at least one processor, cause the at least one processor to perform operations to: compare the set of customer preference probabilities to a sample fragrance library to select a set of fragrance samples for the user; generate a notification message for the user with a recommendation notification that includes identification of the set of fragrance samples; and transmit a notification message to a device of the user.

In Example 55, the subject matter of Examples 47-54 includes, instructions that, when executed by the at least one processor, cause the at least one processor to perform operations to: obtain a genetic profile for the user; obtain an ingredient list for the fragrance; evaluate the genetic profile to generate a prediction of an allergic rection to an ingredient in the ingredient list; prevent recommendation of the fragrance based on the prediction of the allergic reaction; and select an alternate fragrance based on the genetic profile and the set of customer preference probabilities.

In Example 56, the subject matter of Examples 47-55 includes, instructions that, when executed by the at least one processor, cause the at least one processor to perform operations to: obtain a genetic profile for the user; evaluate the genetic profile to identify genetic customer attribute features; and add the genetic customer attribute features to the customer attribute features.

In Example 57, the subject matter of Examples 47-56 includes, instructions that, when executed by the at least one processor, cause the at least one processor to perform operations to: extract social media data from the user data; identify social media profiles using the social media data; obtain characteristic data using the social media profiles; extract social media attribute features from the characteristic data; and add the social media attribute features to the customer attribute features.

In Example 58, the subject matter of Examples 47-57 includes, instructions that, when executed by the at least one processor, cause the at least one processor to perform operations to: obtain environmental condition data for an environment of the user; extract environmental attribute features from the environmental condition data; and add the environmental attribute features to the customer attribute features.

In Example 59, the subject matter of Examples 47-58 includes, instructions that, when executed by the at least one processor, cause the at least one processor to perform operations to: evaluate the customer attribute features to assign the user to a preference group; and select the fragrance recommendation using the set of customer preference probabilities and the preference group.

In Example 60, the subject matter of Examples 47-59 includes, instructions that, when executed by the at least one processor, cause the at least one processor to perform operations to: obtain a video feed from the sensor array; process the video feed using an artificial intelligence processor to identify an emotional reaction of the user to a stimuli present in the video feed; generate an emotive reaction attribute feature for the user based on the identified emotional reaction; and add the emotive reaction feature to the customer attribute features.

In Example 61, the subject matter of Examples 47-60 includes, instructions that, when executed by the at least one processor, cause the at least one processor to perform operations to: collect an air sample using a volatile organic compound (VOC) sensor; evaluate the air sample to identify concentrations of a set of VOCs; query the fragrance database using the concentrations of the set of VOCs to identify a present fragrance; obtain fragrance attribute features for the present fragrance from the fragrance database; and add the fragrance attribute features to the customer attribute features.

In Example 62, the subject matter of Examples 47-61 includes, instructions that, when executed by the at least one processor, cause the at least one processor to perform operations to: obtain social proximity data for the user; evaluate the social proximity data to identify a connection between the user and a connection; collect connection data for the connection; extract connection attribute features from the connection data; and add the connection attribute features to the customer attribute features.

In Example 63, the subject matter of Examples 47-62 includes, instructions that, when executed by the at least one processor, cause the at least one processor to perform operations to: calculate a first correlation coefficient for a first feature of the customer attribute features and a second correlation coefficient for a second feature of the customer attribute features; determine that the first correlation coefficient is outside a correlation coefficient threshold and the second correlation coefficient is within the correlation coefficient; ignore the second feature; and evaluate the first feature using the fragrance recommendation model.

In Example 64, the subject matter of Examples 47-63 includes, instructions that, when executed by the at least one processor, cause the at least one processor to perform operations to: transmit, to an output device of the user computing device, a response request prompt in conjunction with the fragrance recommendation; receive, via an input device of the user computing device, a response to the response request; establish a second recommendation pathway to evaluate the fragrance database using preference parameters determined from the response; evaluate the fragrance database using the preference parameters to select an alternate fragrance recommendation; and output the alternate fragrance recommendation to the user via a display of the user computing device.

In Example 65, the subject matter of Examples 47-64 wherein, the customer attribute features include at least one human parameter and at least one non-human parameter.

In Example 66, the subject matter of Examples 47-65 includes, instructions that, when executed by the at least one processor, cause the at least one processor to perform operations to: transmit, to an output device of the user computing device, a feedback request prompt in conjunction with the fragrance recommendation; receive, via an input device of the user computing device, feedback regarding the fragrance recommendation from the user; and refine the fragrance recommendation model using the feedback.

In Example 67, the subject matter of Examples 47-66 includes, instructions that, when executed by the at least one processor, cause the at least one processor to perform operations to: identify an event in the user data; evaluate the user data to collect event data; extract event attribute features from the event data; and add the event attribute features to the customer attribute features.

In Example 68, the subject matter of Examples 47-67 includes, instructions that, when executed by the at least one processor, cause the at least one processor to perform operations to: train a personality fragrance prediction model using a corpus of training data including personality traits and corresponding fragrance preferences; evaluate a fragrance attribute of a fragrance from the fragrance database using the personality fragrance prediction model to predict one or more personality traits associated with the fragrance attribute; and store the predicted one or more personality traits associated with the fragrance attribute in the fragrance database.

Example 69 is at least one machine-readable medium including instructions that, when executed by processing circuitry, cause the processing circuitry to perform operations to implement of any of Examples 1-68.

Example 70 is an apparatus comprising means to implement of any of Examples 1-68.

Example 71 is a system to implement of any of Examples 1-68.

Example 72 is a method to implement of any of Examples 1-68.

What is claimed is:

1. A method executable by computing circuitry comprising:

collecting sensor data from a sensor array of a user computing device, the sensor array comprising a camera, a microphone, and a volatile organic compound (VOC) sensor, the sensor data comprising attributes of a user in a current environment;

collecting an air sample using the VOC sensor;

evaluating the air sample to identify concentrations of a set of VOCs;

obtaining user data for the user associated with the user computing device;

extracting customer attribute features from the sensor data and the user data;

querying a fragrance database using the concentrations of the set of VOCs to identify a present fragrance;

obtaining fragrance attribute features for the present fragrance from the fragrance database;

adding the fragrance attribute features to the customer attribute features;

establishing a first recommendation pathway to evaluate the customer attribute features using a fragrance recommendation model to calculate a set of customer preference probabilities for fragrances in the fragrance database, wherein the set of customer preference probabilities are calculated as correlation coefficients; and outputting a fragrance recommendation to the user, via a display of the user computing device, based on the set of customer preference probabilities, wherein the fragrance recommendation is selected from a fragrance database comprising correlations between customer attributes and fragrance attributes.

2. The method of claim 1, further comprising:

obtaining fragrance user characteristic training data; and training the fragrance recommendation model to calculate customer preference probabilities for fragrances based on customer characteristics using the fragrance user characteristic training data.

3. The method of claim 1, further comprising:

evaluating the sensor data to determine a current emotional state of the user; and adding the current emotional state to the customer attribute features.

4. The method of claim 1, wherein the user computing device is a mobile computing device, a smartphone, a tablet computing device, a laptop computing device, a desktop computing device, or a kiosk.

5. The method of claim 1, further comprising:

in response to presentation of a stimuli to the user via the display, capturing reaction data from the sensor array;

extracting reaction attribute features from the reaction data; and evaluating the reaction attribute features in conjunction with the customer attribute features to calculate the set of customer preference probabilities.

6. The method of claim 1, wherein the user data includes a gender of the user, hobbies of the user, personality traits of the user, fragrance preferences of the user, purchase history of the user, or product feedback submitted by the user.

7. The method of claim 1, further comprising:

obtaining an image of the user from the sensor data;

detecting facial features in the image;

evaluating the facial features to determine a customer attribute feature; and adding the customer attribute feature to the customer attribute features.

8. The method of claim 1, further comprising:

comparing the set of customer preference probabilities to a sample fragrance library to select a set of fragrance samples for the user;

generating a notification message for the user with a recommendation notification that includes identification of the set of fragrance samples; and transmitting the notification message to a device of the user.

9. The method of claim 1, further comprising:

obtaining a genetic profile for the user;

obtaining an ingredient list for a fragrance included in the fragrance recommendation;

evaluating the genetic profile to generate a prediction of an allergic reaction to an ingredient in the ingredient list;

preventing recommendation of the fragrance based on the prediction of the allergic reaction; and selecting an alternate fragrance based on the genetic profile and the set of customer preference probabilities.

10. The method of claim 1, further comprising:

obtaining a genetic profile for the user;

evaluating the genetic profile to identify genetic customer attribute features; and adding the genetic customer attribute features to the customer attribute features.

11. The method of claim 1, further comprising:

extracting social media data from the user data;

identifying social media profiles using the social media data;

obtaining characteristic data using the social media profiles;

extracting social media attribute features from the characteristic data; and adding the social media attribute features to the customer attribute features.

12. The method of claim 1, further comprising:

obtaining environmental condition data for the current environment of the user;

extracting environmental attribute features from the environmental condition data; and adding the environmental attribute features to the customer attribute features.

13. The method of claim 1, further comprising:

evaluating the customer attribute features to assign the user to a preference group; and selecting the fragrance recommendation using the set of customer preference probabilities and the preference group.

14. The method of claim 1, further comprising:

obtaining a video feed from the sensor array;

processing the video feed using an artificial intelligence processor to identify an emotional reaction of the user to a stimuli present in the video feed;

generating an emotive reaction attribute feature for the user based on the identified emotional reaction; and adding the emotive reaction attribute feature to the customer attribute features.

15. The method of claim 1, further comprising:

obtaining social proximity data for the user;

evaluating the social proximity data to identify a connection between the user and a connection;

collecting connection data for the connection;

extracting connection attribute features from the connection data; and adding the connection attribute features to the customer attribute features.

16. The method of claim 1, further comprising:

calculating a first correlation coefficient for a first feature of the customer attribute features and a second correlation coefficient for a second feature of the customer attribute features;

determining that the first correlation coefficient is outside a correlation coefficient threshold and the second correlation coefficient is within the correlation coefficient threshold;

ignoring the second feature; and evaluating the first feature using the fragrance recommendation model.

17. The method of claim 1, further comprising:

transmitting, to an output device of the user computing device, a response request prompt in conjunction with the fragrance recommendation;

receiving, via an input device of the user computing device, a response to the response request prompt;

establishing a second recommendation pathway to evaluate the fragrance database using preference parameters determined from the response;

evaluating the fragrance database using the preference parameters to select an alternate fragrance recommendation; and outputting the alternate fragrance recommendation to the user via a display of the user computing device.

18. The method of claim 1, wherein the customer attribute features include at least one human parameter and at least one non-human parameter.

19. The method of claim 1, further comprising:

transmitting, to an output device of the user computing device, a feedback request prompt in conjunction with the fragrance recommendation;

receiving, via an input device of the user computing device, feedback regarding the fragrance recommendation from the user; and refining the fragrance recommendation model using the feedback.

* * * * *